US010233134B2

(12) United States Patent
Krolikowski et al.

(10) Patent No.: US 10,233,134 B2
(45) Date of Patent: Mar. 19, 2019

(54) ANTI-FUNGAL SEED TREATMENT FORMULATIONS, TREATED SEEDS, AND METHODS

(71) Applicant: GERMAINS SEED TECHNOLOGY, INC., Gilroy, CA (US)

(72) Inventors: Dale Allan Krolikowski, Salinas, CA (US); David Cross, Salinas, CA (US); Eugenia Tang, San Jose, CA (US)

(73) Assignee: GERMAINS SEED TECHNOLOGY, INC., Gilroy, CA (US)

( * ) Notice: Subject to any disclaimer, the term of this patent is extended or adjusted under 35 U.S.C. 154(b) by 0 days.

(21) Appl. No.: 15/878,704

(22) Filed: Jan. 24, 2018

(65) Prior Publication Data

US 2018/0208517 A1    Jul. 26, 2018

Related U.S. Application Data

(60) Provisional application No. 62/450,020, filed on Jan. 24, 2017.

(51) Int. Cl.
| | | |
|---|---|---|
| *A01N 59/00* | (2006.01) | |
| *A01N 59/20* | (2006.01) | |
| *C05G 3/02* | (2006.01) | |
| *C05D 9/02* | (2006.01) | |
| *A01N 25/00* | (2006.01) | |

(52) U.S. Cl.
CPC .............. *C05G 3/02* (2013.01); *A01N 25/00* (2013.01); *A01N 59/20* (2013.01); *C05D 9/02* (2013.01)

(58) Field of Classification Search
None
See application file for complete search history.

(56) References Cited

U.S. PATENT DOCUMENTS

| 5,504,055 | A  | 4/1996  | Hsu |
| 7,786,614 | B2 | 8/2010  | Sato |
| 8,232,228 | B2 | 7/2012  | Wei |
| 8,481,458 | B2 | 7/2013  | Miles |
| 8,492,312 | B2 | 7/2013  | Thomas |
| 8,632,811 | B1 | 1/2014  | Santra |
| 8,778,371 | B2 | 7/2014  | Yamashita |
| 9,018,133 | B2 | 4/2015  | Seitz et al. |
| 9,144,238 | B2 | 9/2015  | Hoffmann et al. |
| 9,167,818 | B2 | 10/2015 | Gary |
| 9,198,423 | B2 | 12/2015 | Göhlich et al. |
| 9,271,502 | B2 | 3/2016  | Sabin |
| 9,326,522 | B2 | 5/2016  | Misumi |
| 9,370,186 | B2 | 6/2016  | Schirring et al. |
| 2008/0004177 | A1 | 1/2008  | Pfeiffer et al. |
| 2011/0033436 | A1 | 2/2011  | Chen et al. |
| 2011/0124501 | A1 | 5/2011  | Cristau et al. |
| 2011/0306502 | A1 | 12/2011 | Shah et al. |
| 2012/0027741 | A1 | 2/2012  | Coqueron et al. |
| 2014/0378514 | A1 | 12/2014 | Krieg et al. |
| 2015/0216163 | A1 | 8/2015  | Hellwege et al. |
| 2015/0223452 | A1 | 8/2015  | Wachendorff-neumann et al. |
| 2015/0272126 | A1 | 10/2015 | Margolis |
| 2015/0296802 | A1 | 10/2015 | Wachendorff-neumann et al. |
| 2015/0327549 | A1 | 11/2015 | Wachendorff-neumann et al. |
| 2016/0192643 | A1 | 7/2016  | Stark et al. |

FOREIGN PATENT DOCUMENTS

| CN | 102792971 A | 11/2012 |
| CN | 104 876 674 A | 9/2015 |
| EP | 1961306 A1 | 8/2008 |
| EP | 2006288 A1 | 12/2008 |
| EP | 2014165 A1 | 1/2009 |
| EP | 2494867 A1 | 9/2012 |
| EP | 2524598 A1 | 11/2012 |
| EP | 2524599 A1 | 11/2012 |
| EP | 2524600 A1 | 11/2012 |
| EP | 2524601 A1 | 11/2012 |
| EP | 2997825 A1 | 3/2016 |
| WO | WO 2012/045680 A2 | 4/2012 |
| WO | WO 2012/089724 A1 | 7/2012 |
| WO | WO 2015/140071 A1 | 9/2015 |

OTHER PUBLICATIONS

"Kocide® 2000, Fungicide," E.I. du Pont Canada Company, Agricultural Products, Mississauga Ontario, Canada, Dec. 17, 2014, 6 pgs.

Avery, M.L., et al., "Field Tests of a Copper-Based Fungicide as a Bird Repellent Rice Seed Treatment," Proceedings of the Sixteenth Vertebrate Pest Conference, Feb. 1994, 6 pgs.

Conceição, G.M., et al., "Physiological and sanitary quality soybean seeds under different chemical treatments during storage," Revista Brasileira de Engenharia Agrícola e Ambiental, 2016, 20(11);1020-1024, 5 pgs.

Farooq, M., et al., "Micronutrient application through seed treatments—a review," Journal of Soil Science and Plant Nutrition, 2012, 12(1):125-142, 18 pgs.

Kasselaki, A.-M., et al., "Effect of alternative strategies for the disinfection of tomato seed infected with bacterial canker (*Clavibacter michiganensis* subsp. *michiganensis*)," NJAS—Wageningen Journal of Life Sciences, 2011, 58:145-147, 3 pgs.

(Continued)

*Primary Examiner* — Alton N Pryor
(74) *Attorney, Agent, or Firm* — Frost Brown Todd LLC

(57) ABSTRACT

A coated seed comprises a seed and a coating at least partially surrounding the seed. The coating comprises a fungicide, a micronutrient metal, and a chelating agent, the fungicide comprising copper (II) hydroxide, wherein the amount of copper (II) hydroxide is from about 0.05 mg/seed to about 0.21 mg/seed.

A method for applying a seed treatment to a seed or a population of seeds comprises distributing on the surface of the seed or the population of seeds a seed treatment formulation comprising a fungicide, a micronutrient metal, and a chelating agent. The fungicide comprises copper (II) hydroxide in an amount ranging from about 2 wt. % to about 20 wt. % of the total seed treatment formulation.

20 Claims, 15 Drawing Sheets

(56) References Cited

OTHER PUBLICATIONS

International Search Report and Written Opinion dated Apr. 9, 2018 for Application No. PCT/US2018/014993 13 pgs.
Kurnik et al., "Influence of Alternative Copper Fungicide Formulations on Copper Content in Apple Fruits." erwerbs-Obstbau 54.4 (2012): 161-170.
Larsson et al., "Disease Progression and Yield Losses from Root Diseases Caused by Soilborne Pathogens of Spinach," Phytopathology 82.4 (1992) 403-406.
Ruark et al., "Evaluation of Microbial, Botanical, and Organic Treatments for Control of Peanut Seedling Diseases." Plant Disease 94.4 (2010): 445-454.

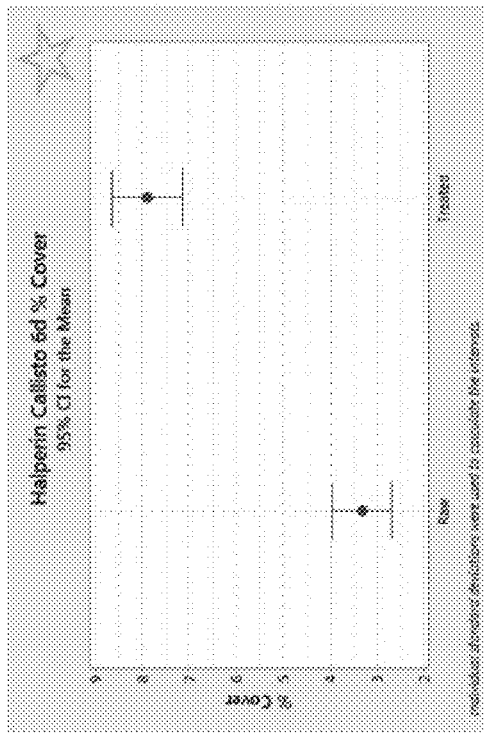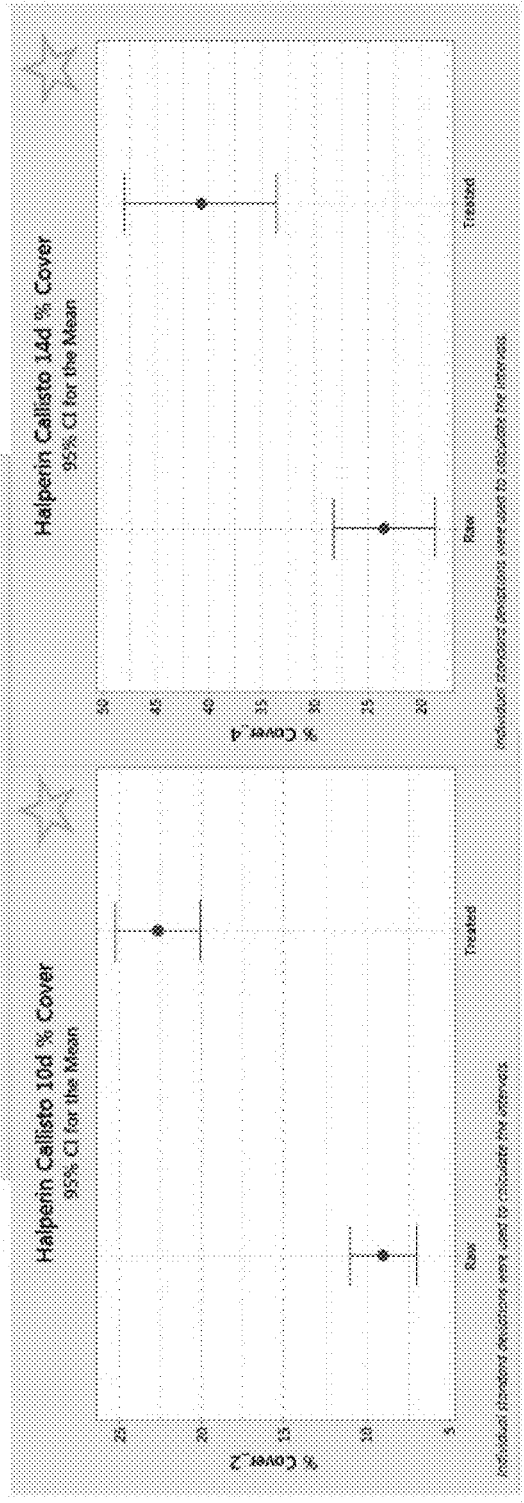
FIG. 7A
FIGS. 7B
FIGS. 7C

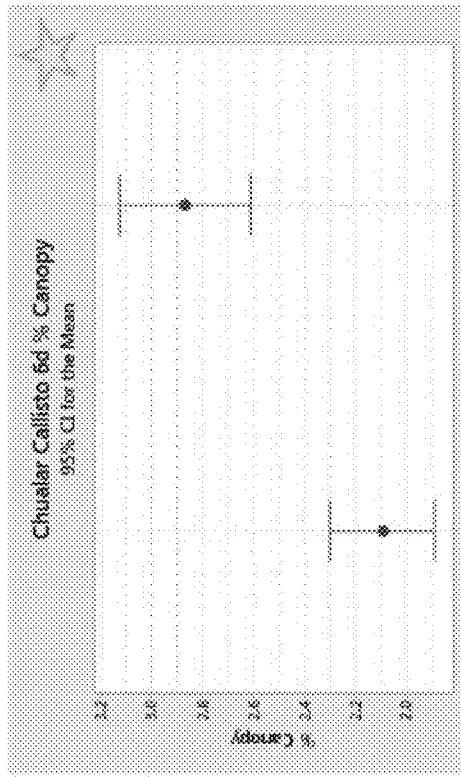
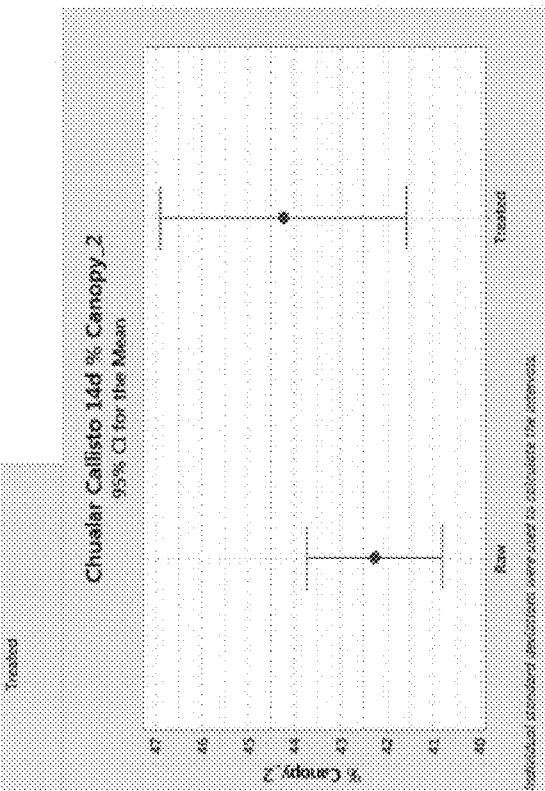
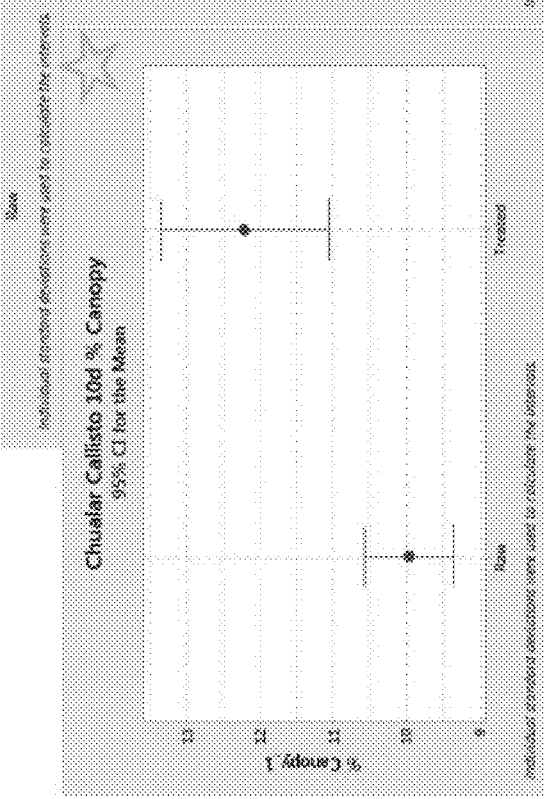
FIG. 13A
FIGS. 13C
FIG. 13B

ANTI-FUNGAL SEED TREATMENT FORMULATIONS, TREATED SEEDS, AND METHODS

CROSS REFERENCE TO RELATED APPLICATIONS

The present application hereby claims the benefit of the provisional patent application of the same title, Ser. No. 62/450,020, filed on Jan. 24, 2017, the disclosure of which is herein incorporated by reference in its entirety.

BACKGROUND

Aspects of the present disclosure generally relate to seed treatment formulations, treated (e.g. coated) seeds, and methods of protecting emerging root systems from fungal growth. In particular, embodiments of the seed treatments described herein are capable of reducing and/or substantially eliminating fungal contaminants from emerging root systems and the surrounding environment, where such fungal contaminants include but are not limited to species of *Fusarium, Pythium*, and *Rhizoctonia*.

The increasing popularity of spinach among consumers has caused a significant increase in the amount of spinach grown in the U.S. in recent years. Persistent pathogenic infection of spinach and other leafy greens in the early stages of development, however, can cause up to a 70% loss in yield (see Larsson et al., "Disease progression and yield losses from root diseases caused by soilborne pathogens of spinach," *Phytopathology* 82:403-406 (1992)), resulting in substantial economic loss for growers and increased food prices for consumers. Specifically, spinach and leafy greens are particularly susceptible to infection by "damping off" complexes and similar root rot diseases, which can cause poor germination and root establishment in infected fields during the first week of development. In infected soils, for example, yield may decrease as the result of desiccation or death of seedlings either pre- or post-emergence, as well as poor overall growth and yellowing of leaves. Susceptibility to such "damping off" and root rot can be exacerbated by poor field conditions, including overwatering, inadequate drainage, and/or crowded planting. While various pathogenic species found in soil can cause "damping off" or root rot, the more common pathogens include fungal species and fungi-like species (oomycetes) of *Fusarium, Pythium*, and *Rhizoctonia*. The poor emergence and/or growth of seedlings due to "damping off" and/or root rot may also affect other crops, including corn, wheat, potato, and soybean, among others.

In general, control of damping off and root rot has been attempted by a variety of methods. One method that may be employed in an effort to reduce or eliminate damping off is to sow seeds in a sterilized growing medium; however, such a method may prove ineffective as fungal spores may be introduced to the growth medium either on the seeds themselves or after sowing (e.g. in water or by wind). Methods requiring sterile growing environments may also be impractical and/or increase costs, particularly for commercial growers managing significant crop acreage. Further methods to prevent damping off include soil drenches, which are not economical due to the fast production cycle where time from planting to harvest is less than 30 days. And, most soil drenches have the added undesirable requirement of long re-entry intervals before workers are permitted to return to the fields.

Another method widely used in the agricultural industry to control fungal infections is the use of fungicides. Fungicides such as metalaxyl (N-(methoxyacetyl)-N-(2,6-xylyl)-DL-alaninate), thiram (dimethylcarbamothioylsulfanyl N,N-dimethylcarbamodithioate), and ipconazole (2-[4 (chlorophenyl)methyl]-5-(1-methylethyl)-1-(1H-1,2,4-trazol-1-ylmethyl)cyclopentanol) have been shown to effectively control fungal infections in emerging root systems, but such use of conventional applied chemistries render these materials unsuitable for the commercial production of organic crops. Copper (II) hydroxide has also found widespread application in the agricultural industry as a fungicide and bactericide. Commercially available in liquid and water dispersible granule form (Champ®, Kocide®), copper (II) hydroxide formulations have, however, traditionally been applied to crop fields by spraying or otherwise coating the leaf surface (i.e. foliar sprays); that is, application occurs post-emergence. Such a contact fungicide in its typical spray form is thus ineffective to treat or prevent soil-borne fungal conditions that invade the emerging root system at the early stages of development (e.g. in the first week after planting).

Current seed treatments marketed for the prevention of damping off and root rot are available, but suffer from significant drawbacks. For the organic market in particular, such seed treatment formulations comprise microbial species, known as bio-pesticides, which are intended to mitigate the effects of insects or disease. Bio-pesticides can be difficult to control under constantly changing environmental conditions, including variations in soil and air temperature, humidity, soil moisture, and nutrient content. The slow growth of these microbial species is similarly problematic, as the microbes may not develop in a manner appropriate to outcompete soil pathogens for root colonization. This slow microbial growth is particularly disadvantageous with respect to *Pythium* and other fungal species, which become established in the emerging root system within just 7 to 10 days after planting.

To address the shortcomings of the methods currently available in the agricultural industry to mitigate or prevent damping off and root rot, it would be advantageous to provide a chemical seed treatment formulation that combines root development nutrition and root protection to combat both pre-emergence and post-emergence fungal infection, where the seed treatment is suitable for use in organic crop production.

BRIEF SUMMARY

Seed treatment formulations for efficiently and cost-effectively protecting seeds and emerging root systems from fungal infections.

In some embodiments, a coated seed comprises a seed and a coating at least partially surrounding the seed. The coating comprises a fungicide, a micronutrient metal, and a chelating agent, the fungicide comprising copper (II) hydroxide, wherein the amount of copper (II) hydroxide is from about 0.05 mg/seed to about 0.21 mg/seed.

In some embodiments, a method for applying a seed treatment to a seed or a population of seeds comprises distributing on the surface of the seed or the population of seeds a seed treatment formulation comprising a fungicide, a micronutrient metal, and a chelating agent. The fungicide comprises copper (II) hydroxide in an amount ranging from about 2 wt. % to about 20 wt. % of the total seed treatment formulation.

In some embodiments, a method of protecting an emerging root system from fungal infection comprises (i) providing at least one seed, (ii) coating the at least one seed with a seed treatment formulation comprising a fungicide, a micronutrient metal, and a chelating agent, (iii) drying the seed treatment formulation to form a coating, and (iv) planting the coated seed under conditions suitable for germination. The fungicide comprises copper (II) hydroxide. The amount of copper (II) hydroxide comprises at least 2 wt. % and no more than about 20 wt. % of the total seed treatment formulation Other aspects and features will be in part apparent and in part described in detail hereinafter.

BRIEF DESCRIPTION OF THE FIGURES

The accompanying drawings, which are incorporated in and constitute a part of this specification, illustrate embodiments, and together with the general description given above, and the detailed description of the embodiments given below, serve to explain the principles of the present disclosure.

FIG. 7A-7F are a series of graphs depicting canopy coverage for raw (i.e. untreated) seed and seed treated with a seed treatment in accordance with the present disclosure, for two spinach varieties at various times after planting at Halperin.

FIG. 13A-13F are a series of graphs depicting canopy coverage for raw (i.e. untreated) seed and seed treated with a seed treatment in accordance with the present disclosure, for two spinach varieties at various times after planting at Chualar.

DETAILED DESCRIPTION

Figure 1:
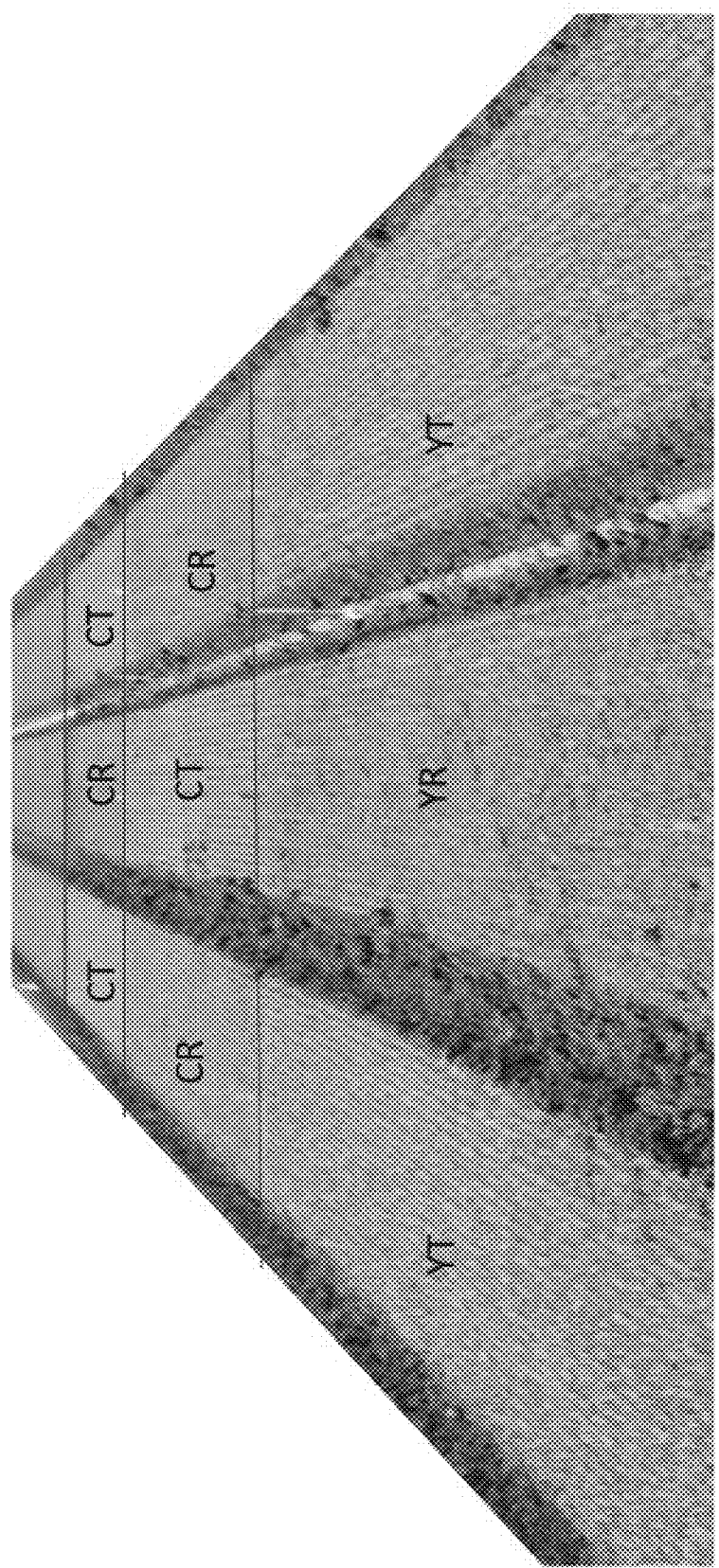
FIG. 1 is a photographic image of Halperin Field Trial, viewed from overhead of randomized split plots planted with spinach seed treated with a seed treatment according to the present disclosure ("CT" and "YT") and untreated spinach seed ("CR" and "YR") at six days after planting at Halperin, as further described in Example 2.
Figure 2:
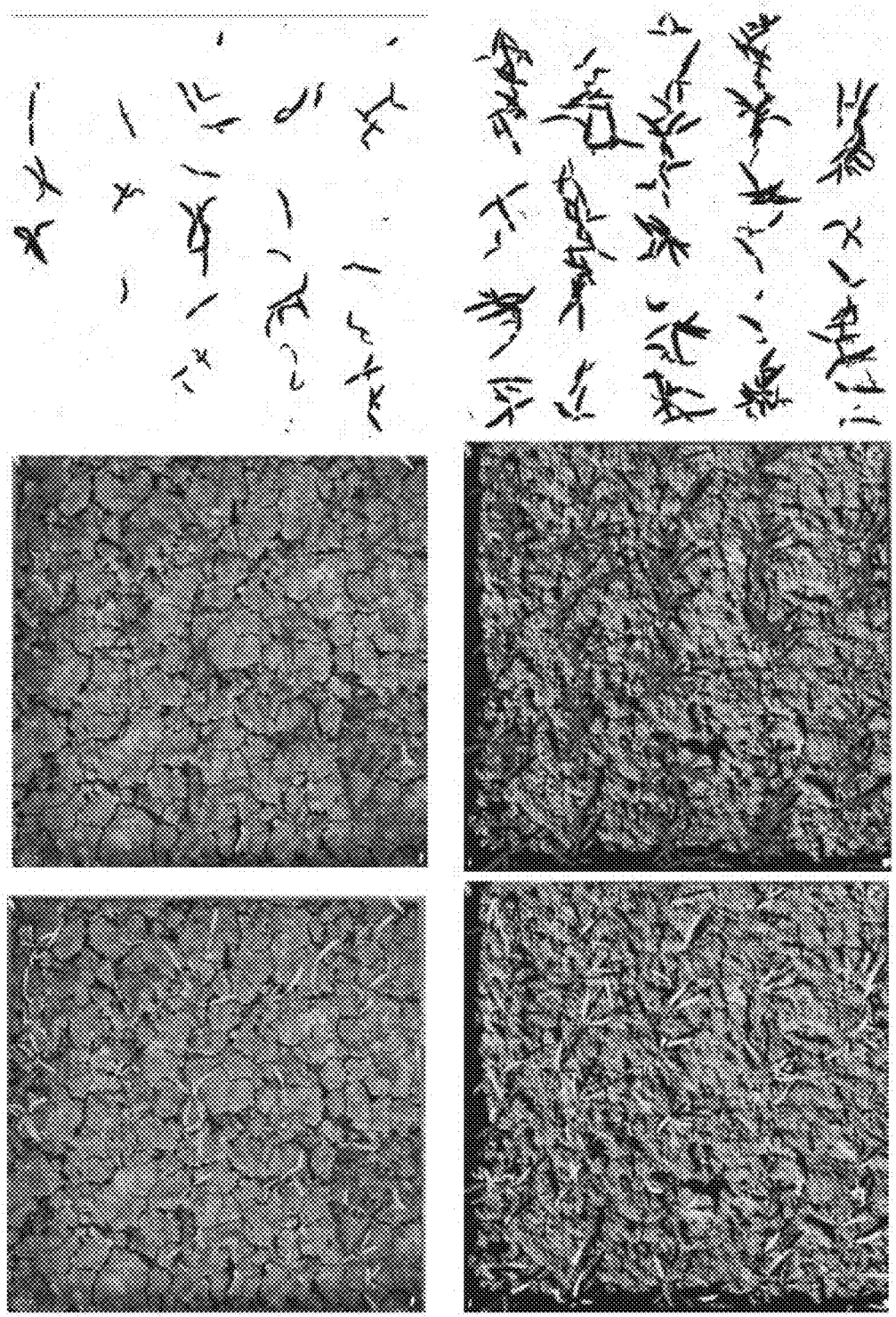
FIG. 2 depicts an image analysis comparing canopy density of raw (i.e. untreated) Callisto spinach seed to Callisto spinach seed treated with a seed treatment according to the present disclosure, shown at six days (6) after planting at Halperin, as further described in Example 2.
Figure 3:
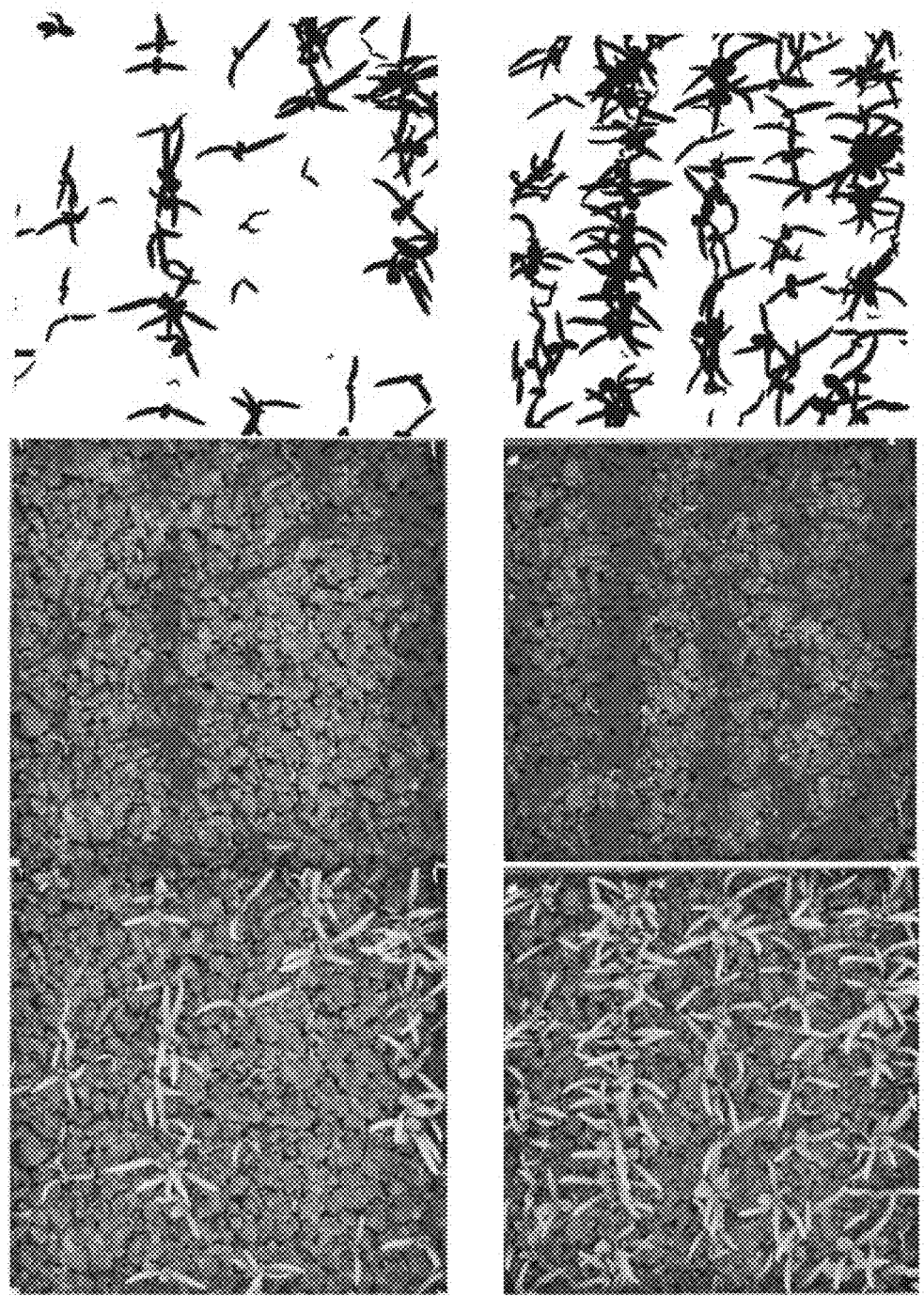
FIG. 3 depicts an image analysis comparing canopy density of raw (i.e. untreated) Callisto spinach seed to Callisto spinach seed treated with a seed treatment according to the present disclosure, shown at ten (10) days after planting at Halperin, as further described in Example 2.
Figure 4:
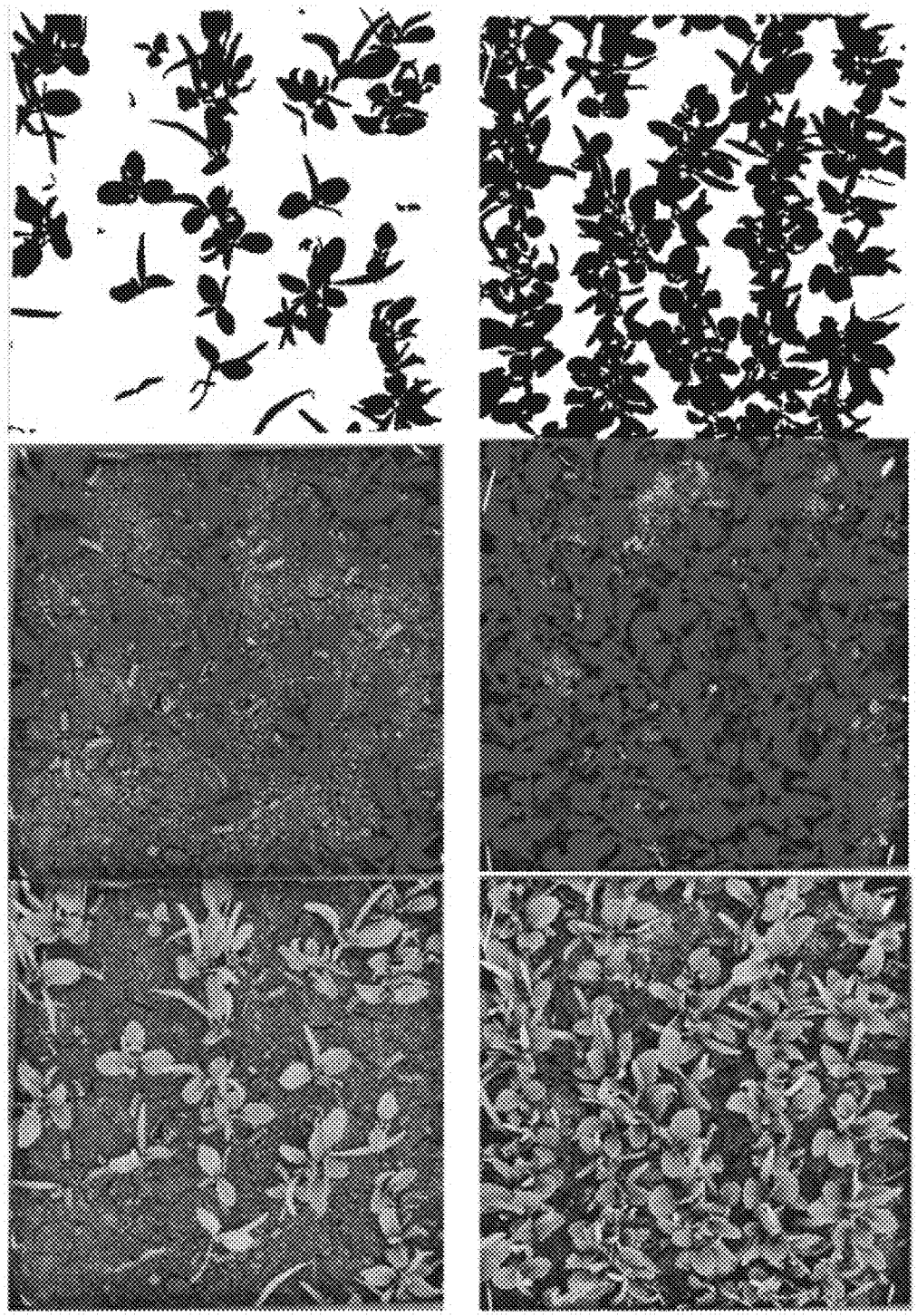
FIG. 4 depicts an image analysis comparing canopy density of raw (i.e. untreated) Callisto spinach seed to Callisto spinach seed treated with a seed treatment according to the present disclosure, shown at fourteen (14) days after planting at Halperin, as further described in Example 2.

Aspects of the present disclosure are directed to a seed treatment formulation for protecting an emerging root system from fungal infection, as well as a seed coated with the formulation and method of using the formulation on seeds. In one aspect, the seed treatment formulation comprises a fungicide comprising copper (II) hydroxide, a micronutrient metal, and a chelating agent. In a further aspect, the copper (II) hydroxide is provided in an amount of at least about 2 wt. % to no more than 20 wt. % of the total seed treatment formulation.

Applicants have surprisingly and unexpectedly found that copper (II) hydroxide, a micronutrient metal, and a chelating agent, when combined in a seed treatment formulation and specifically a seed coating, act synergistically to combat fungal pathogens and strengthen the emerging root system. Without wishing to be bound by any theory, it is believed that the seed treatment formulation is capable of providing protection against fungal species resident in the soil where seeds are planted. In particular, in one aspect, the formulation may be capable of both acting as a fungicide as well as promoting root growth to ensure healthy growth of plants from the planted seed, substantially without succumbing to fungal infection. It is further believed that uptake of the anti-fungal and anti-bacterial agent copper (II) hydroxide is significantly improved by the incorporation of a chelating agent, which both assists in the transport of copper (II) hydroxide across the fungal cell membrane and improves absorption of beneficial micronutrient metals by the emerging plant. Accordingly, the formulations provide a means to offensively attack the fungal pathogen at a cellular level and strengthen the root system in a manner that allows such root system to better defend against pathogenic invasion.

A "seed treatment" according to the present disclosure may be defined as application of a material to a seed prior to or during the time it is planted in soil to improve the characteristics of the seed, protect the seed prior to germination, support the germination and/or support the growth of the resulting plant. In the embodiments of the present disclosure, seed treatments include agricultural active ingredients bound to (e.g. coated onto) a seed or plurality of seeds. "Treating" as used herein refers to any effect, for example, lessening, reducing or modulating, that results in the improvement of the condition, disease, disorder, and the like.

The seed treatment formulation may be effective to mitigate (e.g. lessen the severity of) or prevent a variety of plant diseases and conditions. In particular, the seed treatment formulation may successfully mitigate the effects of, or even prevent, invasion of an emerging root system by fungal containments. In some embodiments, the seed treatment formulation may be effective to mitigate or prevent fungal infection of an emerging root system by one or more species of the following: *Alternaria, Botrytis, Fusarium, Macrophomina, Phyllosticta, Phytophthora, Pseudomonas, Pythium, Rhizoctonia, Sclerotium*, and/or *Thielaviopsis*. In an exemplary embodiment, the seed treatment formulation may be effective to mitigate or prevent fungal infection of an emerging root system by one or more species of *Fusarium, Pythium*, and/or *Rhizoctonia*. In a particularly preferred embodiment, the seed treatment formulation may be effective to mitigate or prevent fungal infection of an emerging root system by *Fusarium oxysporum, Pythium ultimum*, and/or *Rhizoctonia solani*. In yet other embodiments, the seed treatment formulation may also effectively mitigate or prevent bacterial infection of an emerging root system, for example, an infection by the bacterial pathogen *Pseudomonis syringae*.

A coated seed comprises a seed and a coating at least partially surrounding the seed. The coating comprises a fungicide, a micronutrient metal, and a chelating agent, the fungicide comprising copper (II) hydroxide, wherein the amount of copper (II) hydroxide is from about 0.05 mg/seed to about 0.21 mg/seed. In some embodiments, the amount of copper (II) hydroxide is from about 0.05 mg/seed to about 0.21 mg/seed, such as about 0.055 mg/seed to about 0.21 mg/seed, about 0.06 mg/seed to about 0.21 mg/seed, about 0.08 mg/seed to about 0.21 mg/seed, about 0.10 mg/seed to about 0.21 mg/seed, about 0.12 mg/seed to about 0.21 mg/seed, about 0.05 mg/seed to about 0.19 mg/seed, about 0.05 mg/seed to about 0.15 mg/seed, about 0.05 mg/seed to about 0.12 mg/seed, about 0.05 mg/seed to about 0.10 mg/seed, about 0.05 mg/seed to about 0.08 mg/seed, and about 0.05 mg/seed to about 0.06 mg/seed.

In general, a seed treatment formulation in accordance with the present disclosure comprises a fungicide. In some embodiments, the fungicide comprises free copper ion ($Cu^{2+}$). In one exemplary embodiment, the seed treatment formulation comprises copper (II) hydroxide. Commercially available forms of copper (II) hydroxide that may be employed in the disclosed seed treatment formulation include, but are not limited to, Champ® WG (Nufarm Ltd., 77% copper hydroxide) and Kocide® 101 (Certis USA, 77% copper hydroxide). Various concentrations of copper (II) hydroxide may be used in the seed treatment formulation in an amount sufficient to mitigate or prevent fungal infection of an emerging root system. Such amounts may be determined in light of this disclosure and in accordance with methods known to those of skill in the art.

In one embodiment, the seed treatment formulation comprises copper (II) hydroxide in an amount comprising between about 2 wt. % and about 20 wt. % of the total seed treatment formulation. In another embodiment, the seed treatment formulation comprises copper (II) hydroxide in an amount comprising between about 2 wt. % and about 15 wt. % of the total seed treatment formulation. In another embodiment, the seed treatment formulation comprises copper (II) hydroxide in an amount comprising between about 2 wt. % and about 10 wt. % of the total seed treatment formulation. In another embodiment, the seed treatment formulation comprises copper (II) hydroxide in an amount comprising between about 4 wt. % and about 8 wt. % of the total seed treatment formulation. In another embodiment, the seed treatment formulation comprises copper (II) hydroxide in an amount comprising between about 5 wt. % and about 7 wt. % of the total seed treatment formulation. In another embodiment, the seed treatment formulation comprises copper (II) hydroxide in an amount comprising about 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. % or 20 wt. % of the total seed treatment formulation. In another embodiment, the seed treatment formulation comprises copper (II) hydroxide in an amount no less than about 2 wt. % of the total seed treatment formulation. In another embodiment, the seed treatment formulation comprises copper (II) hydroxide in an amount no less than about 4 wt. % of the total seed treatment formulation. In another embodiment, the seed treatment formulation comprises copper (II) hydroxide in an amount no less than about 5 wt. % of the total seed treatment formulation. In another embodiment, the seed treatment formulation comprises copper (II) hydroxide in an amount no more than about 20 wt. % of the total seed treatment formulation. In another embodiment, the seed treatment formulation comprises copper (II) hydroxide in an amount no more than about 17 wt. % of the total seed treatment formulation. In another embodiment, the seed treatment formulation comprises copper (II) hydroxide in an amount no more than about 15 wt. % of the total seed treatment formulation. In another embodiment, the seed treatment formulation comprises copper (II) hydroxide in an amount no more than about 12 wt. % of the total seed treatment formulation. In another embodiment, the seed treatment formulation comprises copper (II) hydroxide in an amount no more than about 10 wt. % of the total seed treatment formulation. In another embodiment, the seed treatment formulation comprises copper (II) hydroxide in an amount no more than about 8 wt. % of the total seed treatment formulation. In another embodiment, the seed treatment formulation comprises copper (II) hydroxide in an amount no more than about 6 wt. % of the total seed treatment formulation.

In general, the seed treatment formulation comprises a micronutrient metal source. Suitable micronutrient sources include zinc, manganese, iron, boron, chromium, cobalt, copper, and molybdenum salts such as phosphates, oxides, sulfates, carbonates, chlorides, nitrates, borates, molybdates and the like and mixtures thereof. For example, the following representative materials may be used as micronutrient sources: zinc sulfate, zinc nitrate, calcium sulfate, calcium nitrate, magnesium sulfate, magnesium nitrate, ferrous sulfate, ferrous nitrate, manganese sulfate, manganese nitrate, copper sulfate, copper nitrate, boric acid, sodium borate, sodium molybdate, ammonium molybdate and the like, either alone or in combination. In a preferred embodiment, the micronutrient source is zinc sulfate.

The seed treatment formulation may be used with all types of seeds. In some embodiments, the treatment formulation is used with spinach, peas, forage corn, sweet corn, and soybeans. In some embodiments, the treatment formulation is used with spinach seeds. In some embodiments, the treatment formulation is used with pea seeds. In some embodiments, the treatment formulation is used with forage corn seeds. In some embodiments, the treatment formulation is used with sweet corn seeds. In some embodiments, the treatment formulation is used with soybean seeds.

In some embodiments, the coated seed is a spinach seed, which comprises a coating at least partially surrounding the seed. The coating comprises a fungicide, a micronutrient metal, and a chelating agent, the fungicide comprising copper (II) hydroxide, wherein the amount of copper (II) hydroxide is from about 0.05 mg/seed to about 0.08 mg/seed.

In some embodiments, the coated seed is a pea seed, which comprises a coating at least partially surrounding the seed. The coating comprises a fungicide, a micronutrient metal, and a chelating agent, the fungicide comprising copper (II) hydroxide, wherein the amount of copper (II) hydroxide is from about 0.1 mg/seed to about 0.21 mg/seed.

In some embodiments, the coated seed is a corn seed, which comprises a coating at least partially surrounding the seed. The coating comprises a fungicide, a micronutrient metal, and a chelating agent, the fungicide comprising copper (II) hydroxide, wherein the amount of copper (II) hydroxide is from about 0.1 mg/seed to about 0.21 mg/seed.

In some embodiments, a seed treatment formulation containing zinc as the only micronutrient may be bound to (e.g. coated on or applied to) a spinach seed. In this embodiment, the seed treatment formulation includes at least about 1.5 wt. % and no more than about 5 wt. % zinc based on the total weight of the seed treatment formulation. In some embodiments, a seed treatment formulation containing iron as the only micronutrient may be bound to a spinach seed. In this embodiment, the seed treatment formulation includes at least about 0.5 wt. % and no more than about 3 wt. % iron, based on the total weight of the seed treatment formulation. In some embodiments, a seed treatment formulation containing manganese as the only micronutrient may be bound to a spinach seed. In this embodiment, the seed treatment formulation includes at least about 0.5 wt. % and no more than about 3 wt. % manganese, based on the total weight of the seed treatment formulation. In some embodiments, a seed treatment formulation containing copper as the only micronutrient may be bound to a spinach seed. In this embodiment, the seed treatment formulation includes at least about 2 wt. % and no more than about 8 wt. % copper, based on the total weight of the seed treatment formulation. In some embodiments, a seed treatment formulation containing chromium as the only micronutrient may be bound to a spinach seed. In this embodiment, the seed treatment formulation includes at least about 0.5 wt. % and no more than about 2 wt. % chromium, based on the total weight of the seed treatment formulation. In some embodiments, a seed treatment formulation containing cobalt as the only micronutrient may be bound to a spinach seed. In this embodiment, the seed treatment formulation includes at least about 0.5 wt. % and no more than about 2 wt. % cobalt, based on the total weight of the seed treatment formulation. In some embodiments, a seed treatment formulation contains at least two different micronutrients, wherein the seed treatment may be bound to a spinach seed. In this embodiment, the seed treatment formulation includes at least about 2 wt. %, total micronutrient, based on the total weight of the seed treatment formulation. Alternatively, the seed treatment formulation comprises at least about 10 wt. %, alternatively at least about 15 wt. %, alternatively at least about 20 wt. %, alternatively at least about 22 wt. %, alternatively at least about 25 wt. %, alternatively at least about 30 wt. %, alternatively at least about 35 wt. %, micronutrients based on the total weight of the seed treatment formulation. Alternately, the composition contains less than about 15 wt. %, less than about 10 wt. %, or less than about 5 wt. % of boron, chromium, cobalt, copper, iodine, iron, manganese, molybdenum, selenium, sulfur and zinc, in combination, again with reference to total weight of the seed treatment formulation. In each of these embodiments, the spinach seeds may be substituted with pea, forage corn, sweet corn, or soybean seeds.

In general, the seed treatment formulation comprises a chelating agent. Without wishing to be bound by any theory, it is believed that the coordinated bonds of the chelating agent holds the micronutrient metal component of the seed treatment formulation so that it remains readily available to the emerging root system. As a result, uptake of the micronutrient metal by the emerging root system is improved leading to additional strength and viability. Use of a chelating agent also advantageously binds copper ion, maintaining the presence of copper ion in the soil and facilitating contact with undesirable fungal pathogens.

In some embodiments, the chelating agent of the seed treatment formulation is zeolite, EDTA, or a combination thereof. In some embodiments, which are suitable for certified organic agricultural applications, the chelating agent of the seed treatment formulation is zeolite. In some embodiments, the seed treatment formulation comprises zeolite in an amount ranging from about 3 wt. % to about 10 wt. %, based on the total weight of the seed treatment formulation. In some embodiments, the seed treatment formulation comprises zeolite in an amount ranging from about 4 wt. % to about 9 wt. %, based on the total weight of the seed treatment formulation. In some embodiments, the seed treatment formulation comprises zeolite in an amount ranging from about 5 wt. % to about 8 wt. %, based on the total weight of the seed treatment formulation. In some embodiments, the seed treatment formulation comprises zeolite in an amount ranging from about 6 wt. % to about 8 wt. %, based on the total weight of the seed treatment formulation. In some embodiments, the seed treatment formulation comprises about 3 wt. %, 4 wt. %, 5 wt. %, 6 wt. %, 7 wt. %, 8 wt. %, 9 wt. % or 10 wt. % zeolite based on the total weight of the seed treatment formulation. These values are significant in that amounts of zeolite less than about 3 wt. % do not provide sufficient chelation effect, while amounts of zeolite greater than about 10 wt. % may result in phytotoxicity.

In general, the seed treatment formulation may comprise one or more additives serving various functions. For example, the seed treatment formulation may comprise a binding agent for improved adherence of the seed treatment formulation to the seed, a humic acid source for improved chelation (in addition to the chelation effect of EDTA or zeolite), a soil conditioner for improved micronutrient availability and uptake, and other additives that may confer a beneficial effect on the emerging root system.

In some embodiments, the seed treatment formulation includes at least one soil conditioner. Soil conditioners may be effective for stimulating antimicrobial activity and improving growing conditions for the seed. One representative soil conditioner that may be employed is BorreGro CA (commercially available from LignoTech AGRO), a purified calcium lignosulfonate product. Typically utilized as a soil-based product, a soil conditioner for use with the seed treatment formulation is adapted for application to (e.g. binding to or coating of) the seed itself rather than being deposited in the surrounding soil.

In some embodiments, the seed treatment formulation may comprise a soil conditioner in an amount ranging from about 0.5 wt. % to about 3 wt. %, based on the total weight of the seed treatment formulation. In other embodiments, the seed treatment formulation may comprise a soil conditioner in an amount ranging from about 1 wt. % to about 2 wt. %, based on the total weight of the seed treatment formulation. In yet other embodiments, the seed treatment formulation may comprise a soil conditioner in an amount ranging from about 0.5 wt. % to about 1.5 wt. %, based on the total weight of the seed treatment formulation. In certain preferred embodiments, the seed treatment formulation may comprise a soil conditioner in the amount no greater than about 3 wt. %, at which point the soil conditioner may have a negative effect on the emerging root system as a result of toxicity.

In certain embodiments, the seed treatment formulation may comprise a binder component. The binder component of the seed treatment formulation may be comprised of an adhesive polymer that may be natural or synthetic and is without phytotoxic effect on the seed to be treated. The binder may be selected from polyvinyl acetates, polyvinyl acetate copolymers, polyvinyl alcohols, polyvinyl alcohol copolymers, celluloses, including ethylcelluloses and methylcelluloses, hydroxymethylcelluloses, hydroxypropyl cellulose, hydroxymethylpropylcelluloses, polyvinylpyrolidones, dextrins, malto-dextrins, polysaccharides, fats, oils, proteins, fiber gums including gum arabics, shellacs, vinylidene chloride, vinylidene chloride copolymers, calcium lignosulfonates, acrylic copolymers, starches, polyvinylacrylates, zeins, gelatin, carboxymethylcellulose, chitosan, polyethylene oxide, acrylimide polymers and copolymers, polyhydroxyethyl acrylate, methylacrylimide monomers, alginate, ethylcellulose, polychloroprene and syrups or mixtures thereof. Preferred binders include polymers and copolymers of vinyl acetate, methyl cellulose, polyvinyl alcohol, vinylidene chloride, acrylic, cellulose, polyvinylpyrrolidone and polysaccharide. Particularly preferred classes of binders include polyvinyl acetates (e.g. for use in conventional growing) and fiber gums (e.g. for use in organic applications).

In one embodiment, the seed treatment formulation may comprise a humic acid source, which functions as a complexing agent for soil nutrients and maintains soil nutrients in forms that are more readily available to the plant. In an exemplary embodiment, the seed treatment formulation comprises humic acid in an amount ranging from about 0.5 wt. % to about 3 wt. % of the total seed treatment formulation. In another exemplary embodiment, the seed treatment formulation comprises humic acid in an amount ranging from about 0.5 wt. % to about 1.5 wt. % of the total seed treatment formulation. In yet another embodiment, the seed treatment formulation comprises about 1 wt. % humic acid based on the total weight of the seed treatment formulation. In certain embodiments, the humic acid source is substantially free of fulvic acid or fulvic acid additives, which yields undesirable precipitates in the seed treatment formulation of the present disclosure.

The seed treatment formulation is applied to the seed and dried to form a coating. The relative amounts of the ingredients in the formulation will be the same as the relative amounts in the coating with the exception of the evaporated water. Any of the described seed treatment ingredients will also be ingredients in the coating.

The seed treatment formulation may be applied to a seed or population of seeds by methods known to those of skill in the art. In particular, the seed treatment formulation may be applied to primed or unprimed seeds, with exemplary priming techniques including hydropriming, solid matrix priming, drum priming, and the like. Primed or unprimed seeds may optionally be dried at a temperature ranging from about 80° F. to about 110° F., to reach a moisture content less than about 50%, 40%, 30%, 20% or even 10%, prior to application of the seed treatment. The seed treatment may be bound to the seed or population of seeds by any one of a variety of seed coating methods, including drum coating, rotary coating, pan coating, fluidized bed coating, and the like. In certain embodiments, treated (i.e. coated) seeds may be put through a second drying process to reduce moisture content of the seed treatment to less than about 25%, 20%, 10%, or even 5%. In some embodiments, the (primed or unprimed) seed(s) to which the seed treatment formulation is applied may be disinfected prior to application using one or more of hot water, warm/moist air, steam, 1% bleach solution, peroxyacetic acid, and the like.

In certain embodiments, the seed(s) may be substantially encapsulated by the seed treatment coating. In another embodiment, at least 95% of the surface area of the seed(s) may be coated with the seed treatment formulation. In yet another embodiment, at least 90% of the surface area of the seed(s) may be coated with the seed treatment formulation. In yet another embodiment, at least 80% of the surface area of the seed(s) may be coated with the seed treatment formulation. In yet another embodiment, at least 75% of the surface area of the seed(s) may be coated with the seed treatment formulation. In yet another embodiment, at least 50% of the surface area of the seed(s) may be coated with the seed treatment formulation.

The seed treatment formulation is used to produce a seed coating effective to protect emerging root systems from fungal infection. In some embodiments, the coating is effective to protect the emerging root system from fungal infection for at least 7 days. By way of further example, the coating is effective to protect the emerging root system from fungal infection for at least 10 days. By way of further example, the coating is effective to protect the emerging root system for at least 12 days. By way of further example, the coating is effective to protect the emerging root system for at least 14 days. By way of further example, the coating is effective to protect the emerging root system for at least 15, 16, 17, 18, 19, 20, or 21 days. The coating may be effective to protect the seed from pre-emergence fungal infection, post-emergence fungal infection, or both pre- and post-emergence fungal infection.

In certain exemplary embodiments, the seed treatment formulation is organic (i.e. certified organic). For a seed treatment formulation to be organic it must satisfy specific governmental standards. These governmental standards vary from country to country. The term "organic" or "certified organic" as used in the pending application is intended to indicate that the seed treatment formulation has satisfied the standards for being denoted as organic in both the United States and the European Union. The United States Department of Agriculture (USDA) regulates organic certification within the United States through a National Organic Program (NOP). To qualify to use the organic label, the requesting organization must be certified as satisfying a variety of guidelines by an NOP accredited certification agency; for example, certification by Agricultural Services Certified Organics, LLC (ASCO).

While the present disclosure has illustrated by description several embodiments and while the illustrative embodiments have been described in considerable detail, it is not the intention of the applicant to restrict or in any way limit the scope of the appended claims to such detail. Additional advantages and modifications may readily appear to those skilled in the art.

EXAMPLES

The following non-limiting examples are provided to further illustrate the present disclosure. It will be apparent to those of skill in the art that the techniques disclosed in the examples that follow represent approaches that function well, and thus can be considered to constitute examples of modes for practice. However, those of skill in the art should, in light of the present disclosure, appreciate that changes can be made in the specific embodiments that are disclosed and still obtain a like or similar result without departing from the spirit and scope of the disclosure.

Example 1

The seed treatment formulation consists of the materials listed in Table 1, which are incrementally mixed, over a period of several minutes, in the indicated amounts to form a solution. The material is fully mixed for an additional 30 minutes before application by film coating to approximately 1.00 lb. of spinach seeds. The coated spinach seeds are subsequently dried to 6-7% moisture content. In this example, while the copper (II) hydroxide used is 77% pure, the weight percent of copper (II) hydroxide is 8.6%

TABLE 1

| Ingredient | Wt. % (Total Formulation) |
| --- | --- |
| Water | 71.4% |
| Zinc Sulfate | 16.2% |
| Lignosulfonate Soil Conditioner | 1.3% |
| Fiber Gum | 1.6% |
| Zeolite | 9.5% |
| Copper (II) Hydroxide (77%) | 8.6% |

Example 2

Randomized 60' split plots were planted with raw spinach seeds (control) and spinach seeds coated with the formulation of Example 1 in a commercial organic field using commercial planting methods. All seeds were sown using commercial planting methods at a depth of 0.5 to 1 cm, in 48 rows on an 80" wide bed at 3-4 million seeds per acre. Spinach varieties Yukon and Castillo are shown in FIG. 1 ("CT"=castillo treated; "CR"=castillo raw; "YT"=yukon treated; "YR"=yukon raw), which illustrates crop density 6 days after planting.

Figure 5:
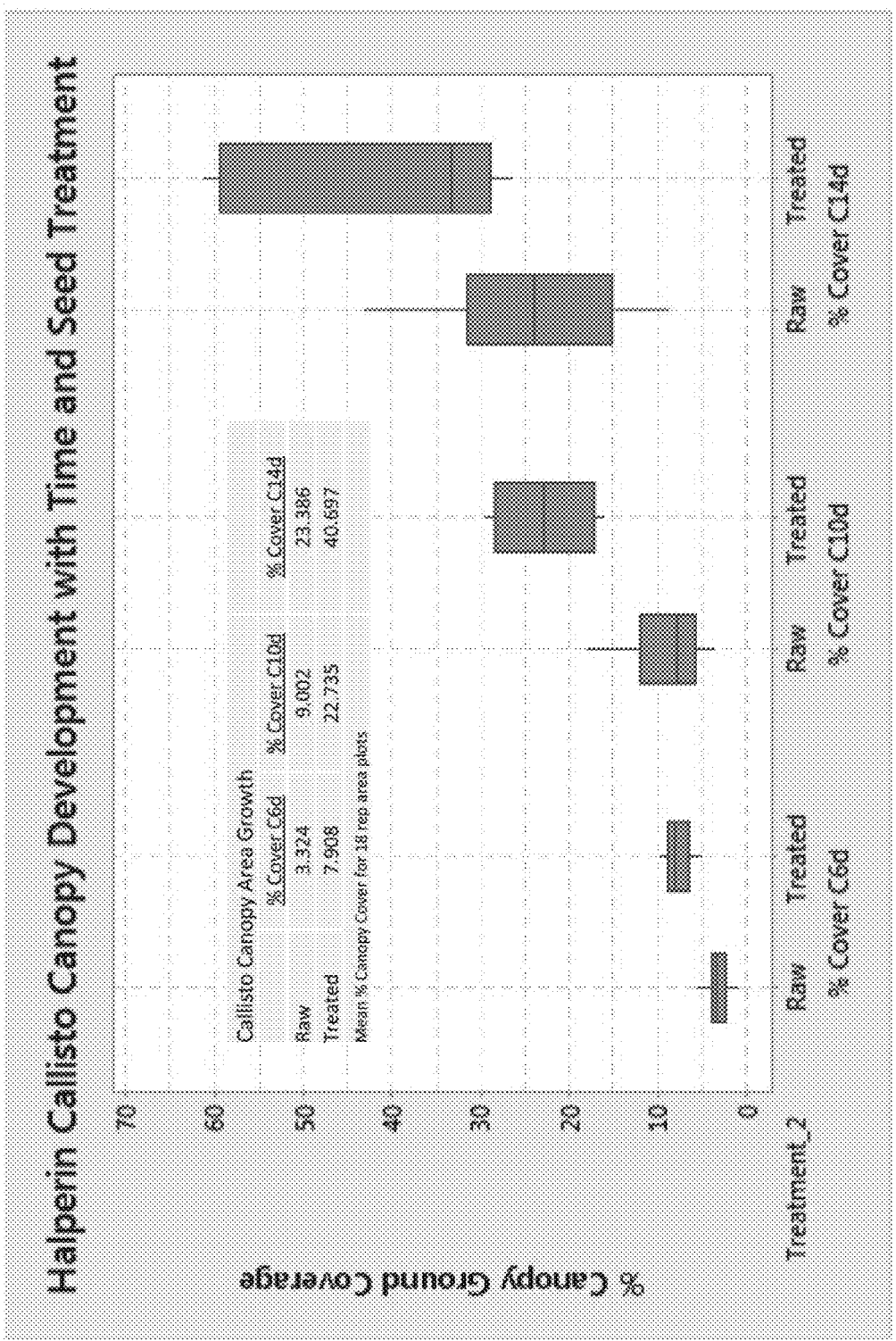
FIG. 5 is a graph depicting the percentages of canopy ground coverage over time for Callisto spinach seed planted at Halperin, comparing raw seed and seed treated with the seed treatment in accordance with the present disclosure, as further described in Example 2.
Figure 6:
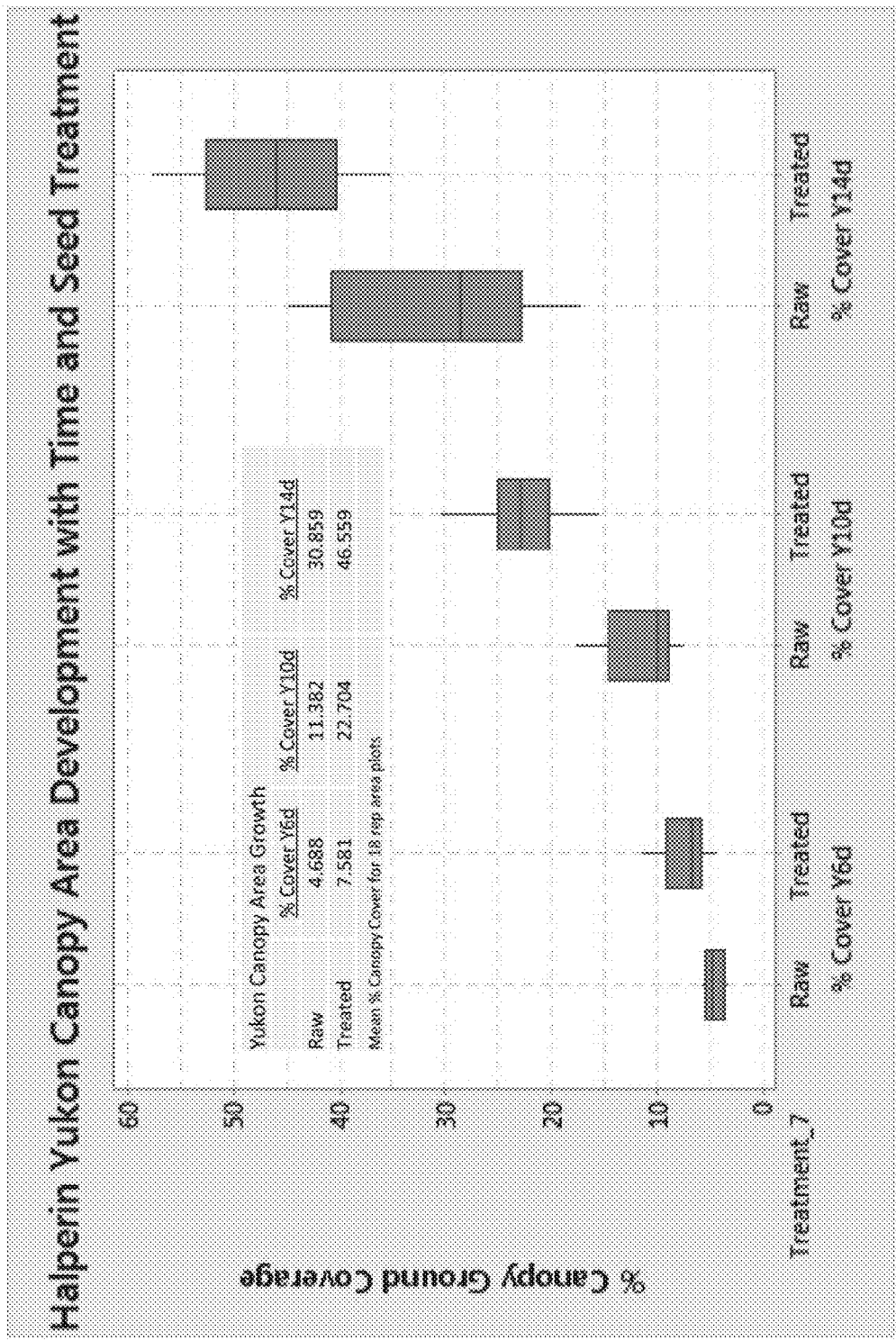
FIG. 6 is a graph depicting the percentages of canopy ground coverage over time for Yukon spinach seed planted at Halperin, comparing raw seed and seed treated with the seed treatment in accordance with the present disclosure, as further described in Example 2.
Figures 7D, 7E, 7F:
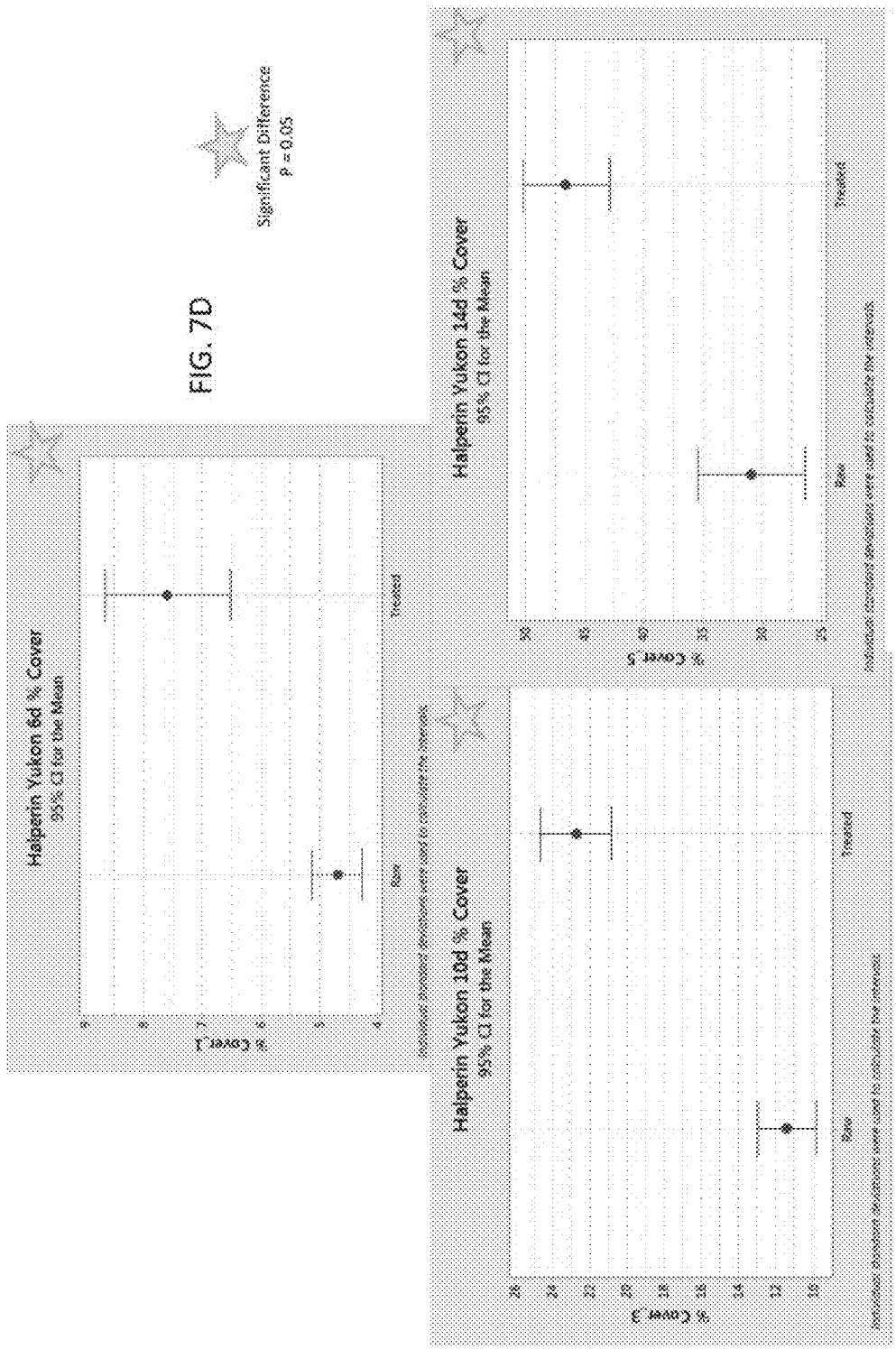

Image analysis of canopy coverage is shown in FIG. 2-7. Images shown in FIGS. 2-4 were taken using software comparable to ImageJ or Canopeo (iPhone-compatible app), with reversal of image color to enable pixel count and subsequent area determination. As shown in FIGS. 5-7, canopy development was significantly (P=0.05) faster with treated spinach seed during first 2 weeks from sowing in both Callisto and Yukon varieties. Additionally, canopy area was significantly larger (P=0.05) and less patchy when treated seed was sown compared with untreated seed.

Example 3

Figure 8:
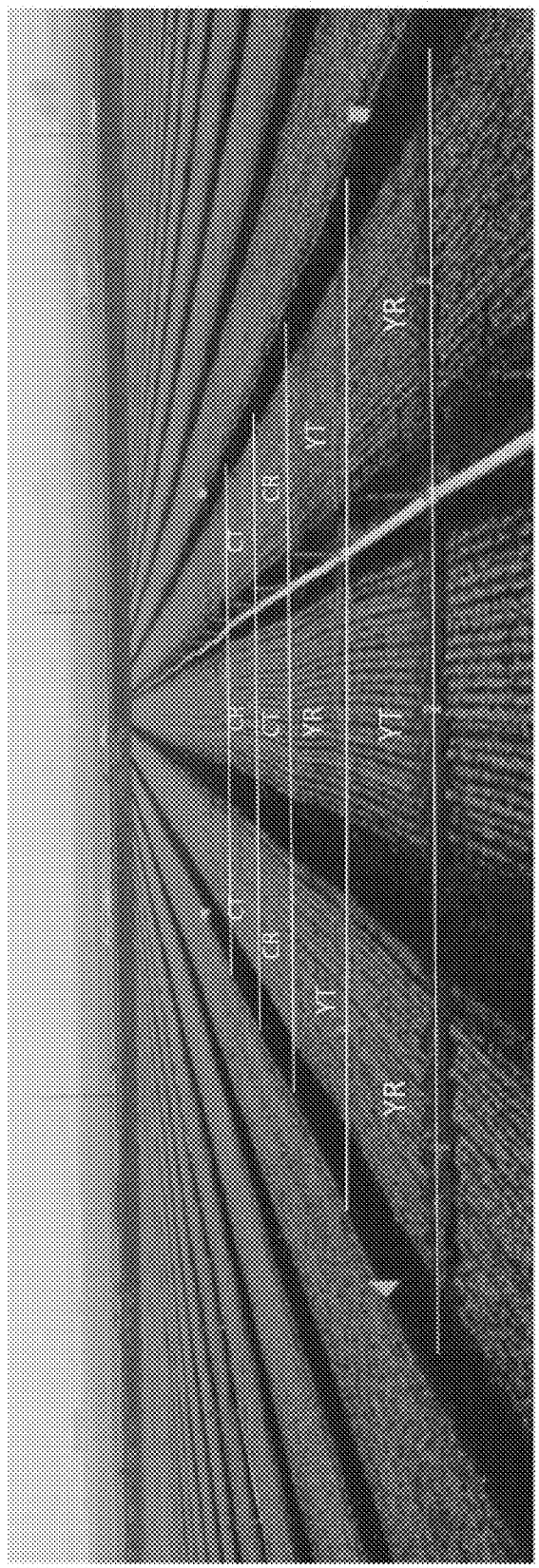
FIG. 8 is a photographic image of Chualar Field Trial, viewed from overhead of randomized split plots planted with spinach seed treated with a seed treatment according to the present disclosure ("CT" and "YT") and untreated spinach seed ("CR" and "YR") at six days after planting at Chualar, as further described in Example 3.
Figure 9:
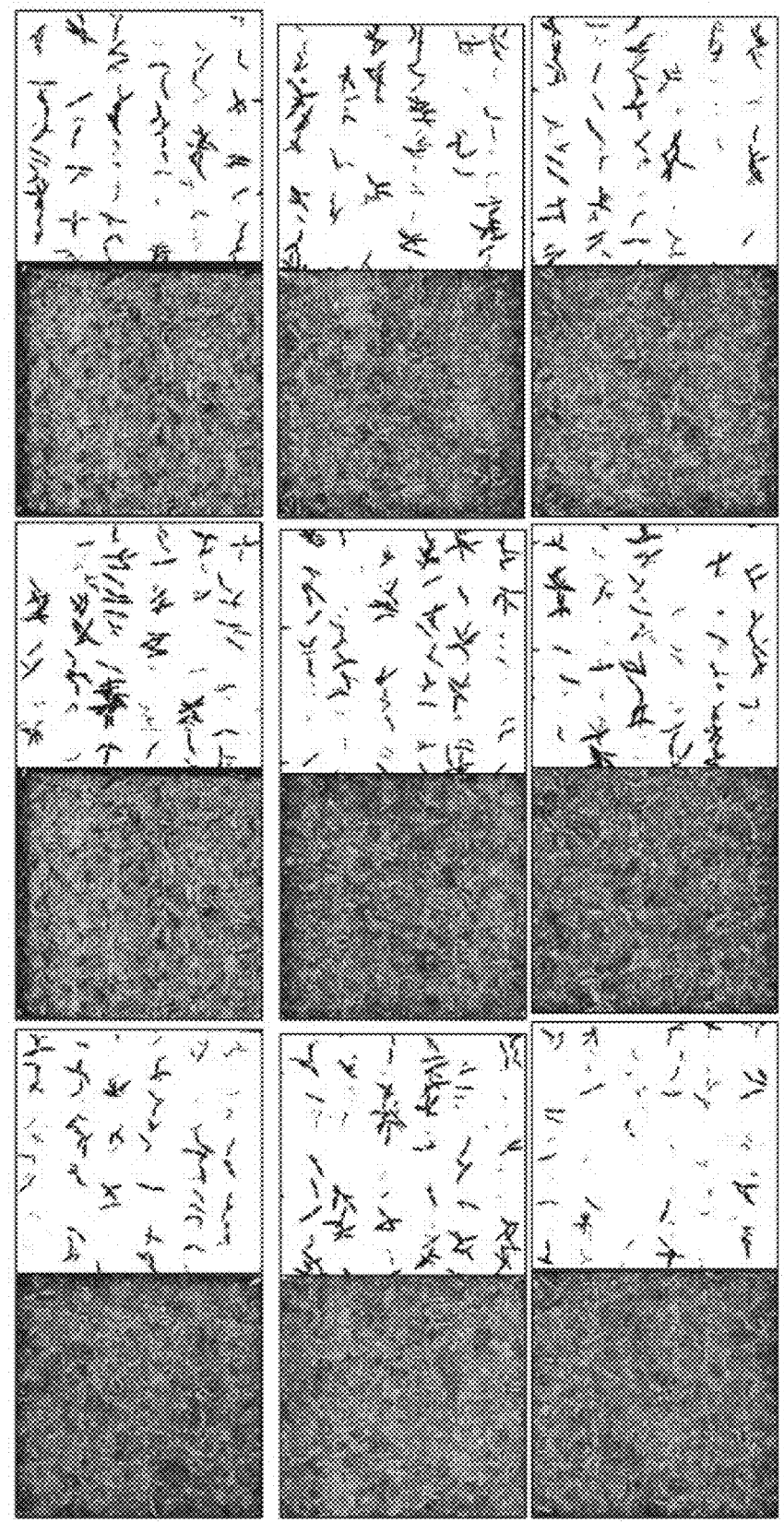
FIG. 9 depicts photographic and reverse images of canopy density of raw (i.e. untreated) Callisto spinach seed shown at ten (10) days after planting at Chualar, as further described in Example 3.
Figure 10:
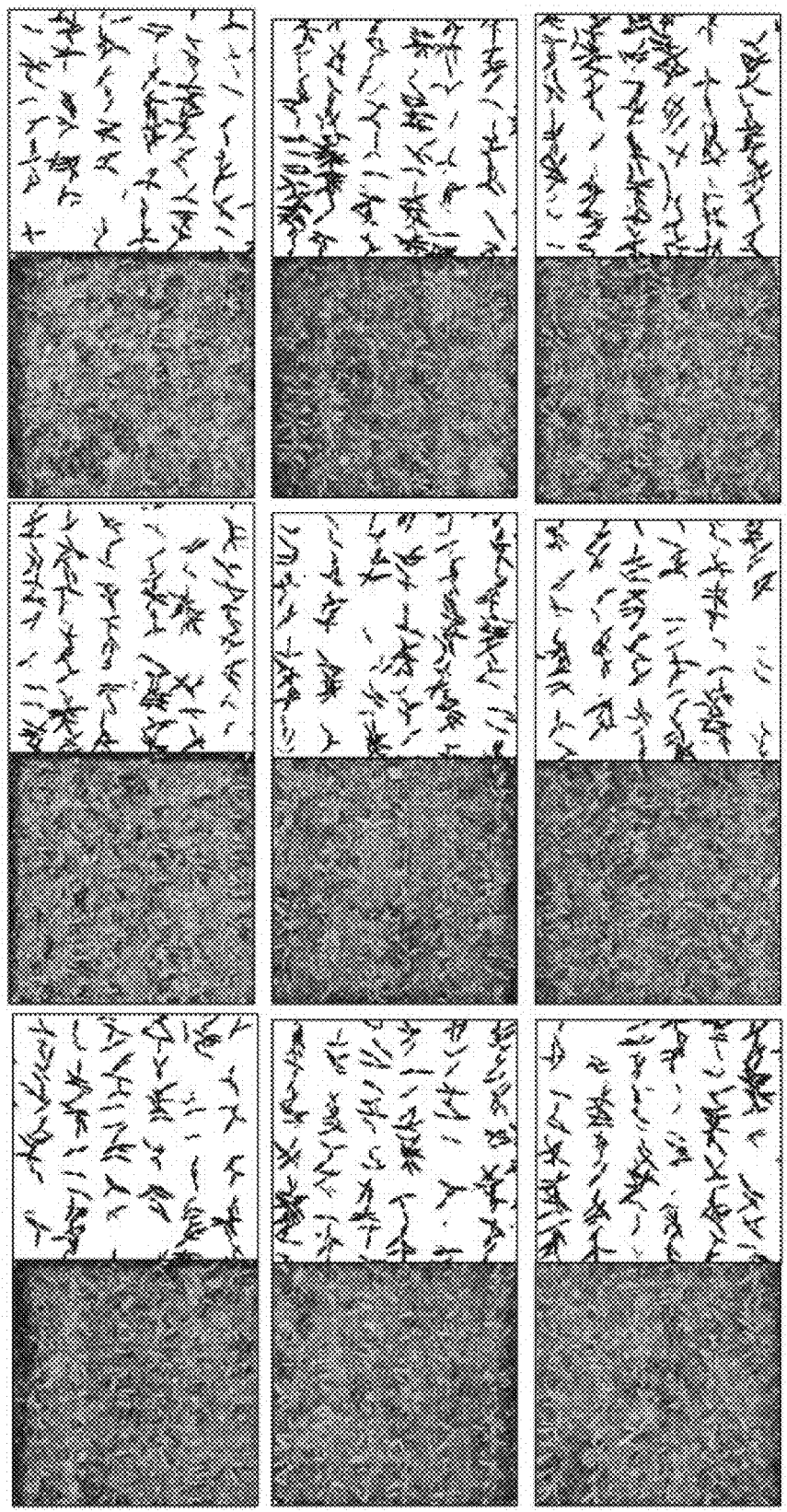
FIG. 10 depicts photographic and reverse images of canopy density of Callisto spinach seed treated with a seed treatment according to the present disclosure, shown at ten (10) days after planting at Chualar, as further described in Example 3.

Randomized 60' split plots were planted with raw spinach seeds (control) and spinach seeds coated with the formulation of Example 1 in a commercial organic field using commercial planting methods. All seeds were sown using commercial planting methods at a depth of 0.5 to 1 cm, in 48 rows on an 80" wide bed at 3-4 million seeds per acre. Spinach varieties Yukon and Castillo are shown in FIG. 8 ("CT"=castillo treated; "CR"=castillo raw; "YT"=yukon treated; "YR"=yukon raw), which illustrates crop density 9 days after planting.

Figure 11:
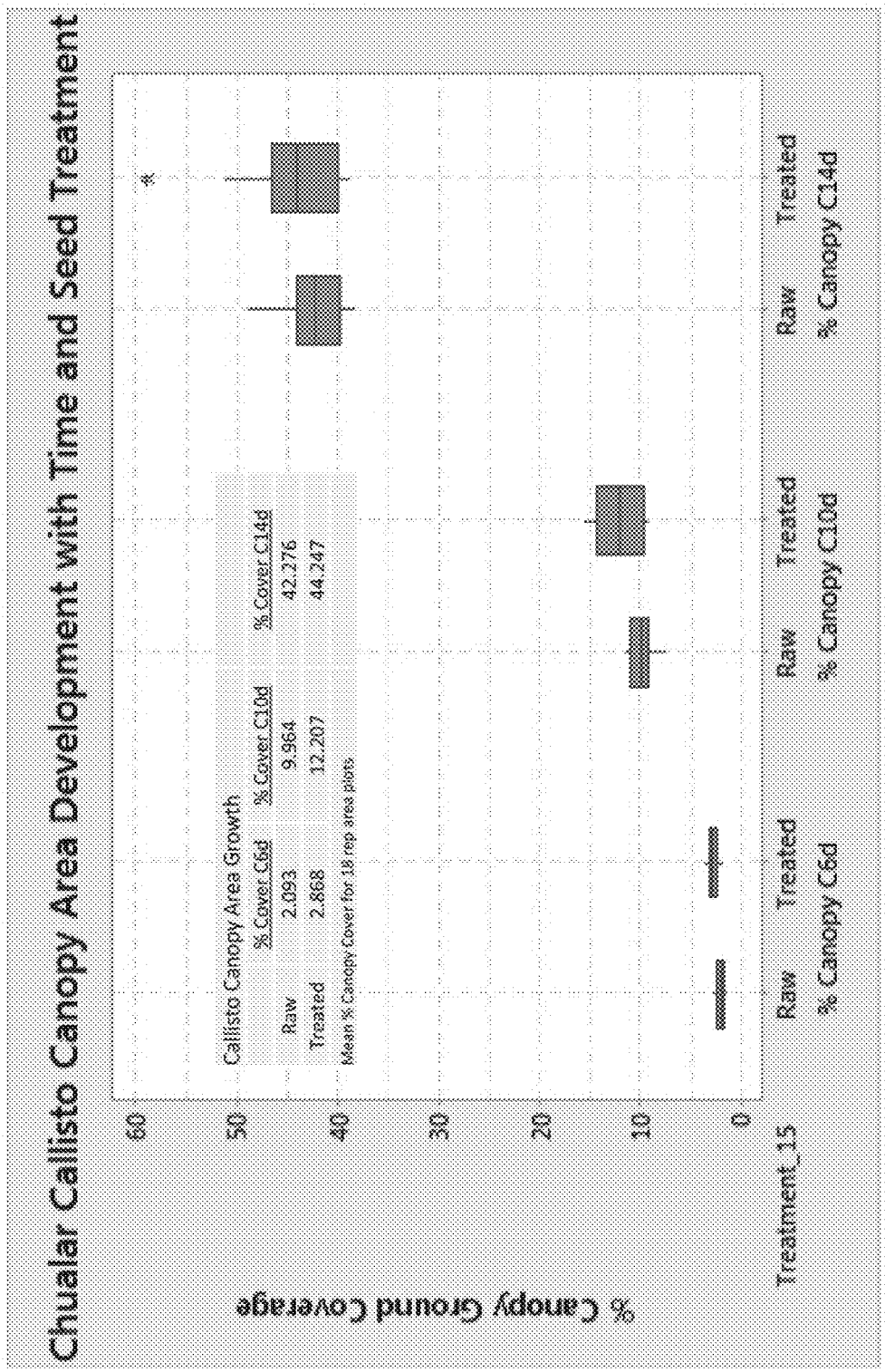
FIG. 11 is a graph depicting the percentages of canopy ground coverage over time for Callisto spinach seed planted at Chualar, comparing raw seed and seed treated with the seed treatment in accordance with the present disclosure, as further described in Example 3.
Figure 12:
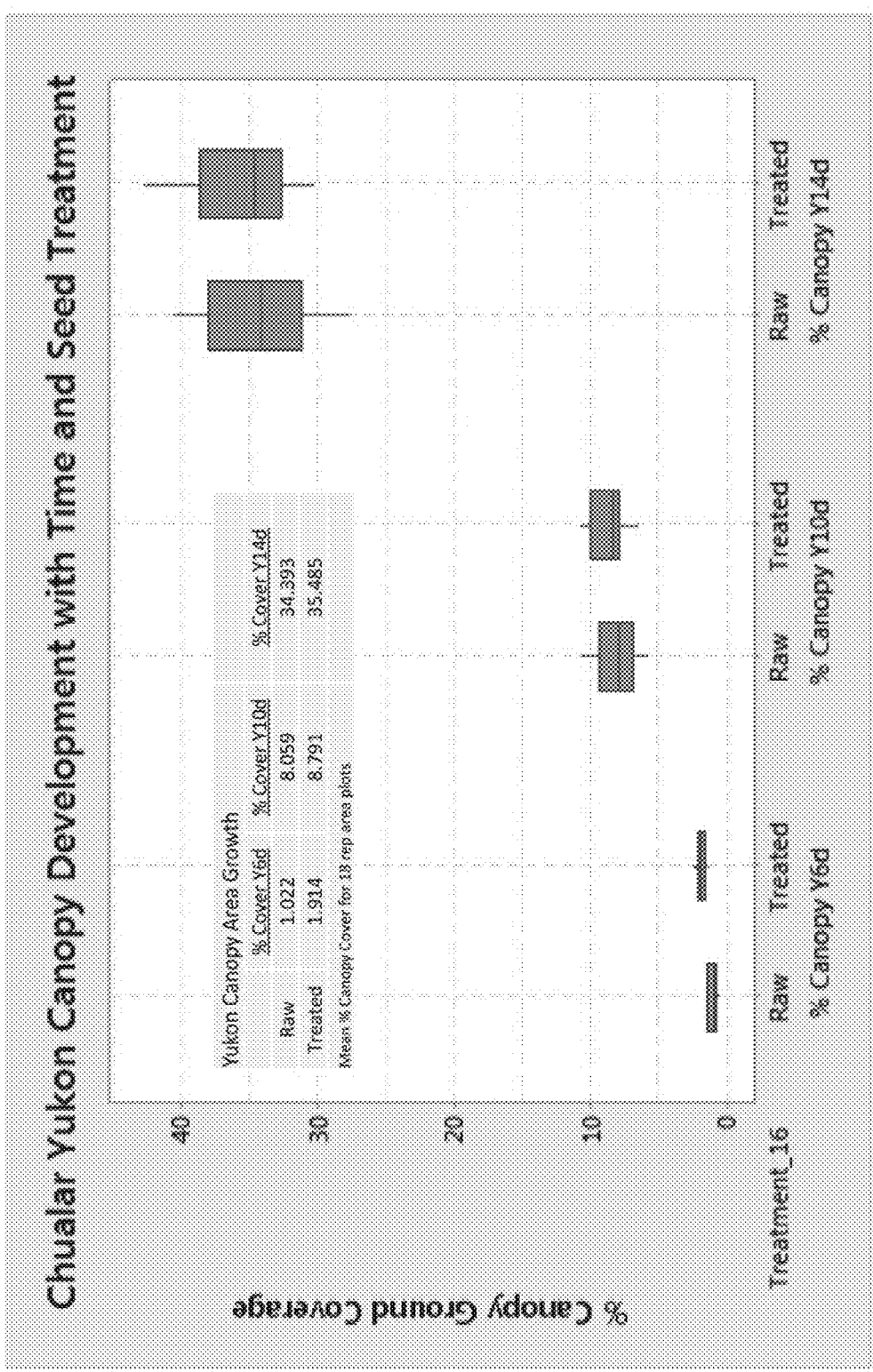
FIG. 12 is a graph depicting the percentages of canopy ground coverage over time for Yukon spinach seed planted at Chualar, comparing raw seed and seed treated with the seed treatment in accordance with the present disclosure, as further described in Example 3.
Figures 13D, 13E, 13F:
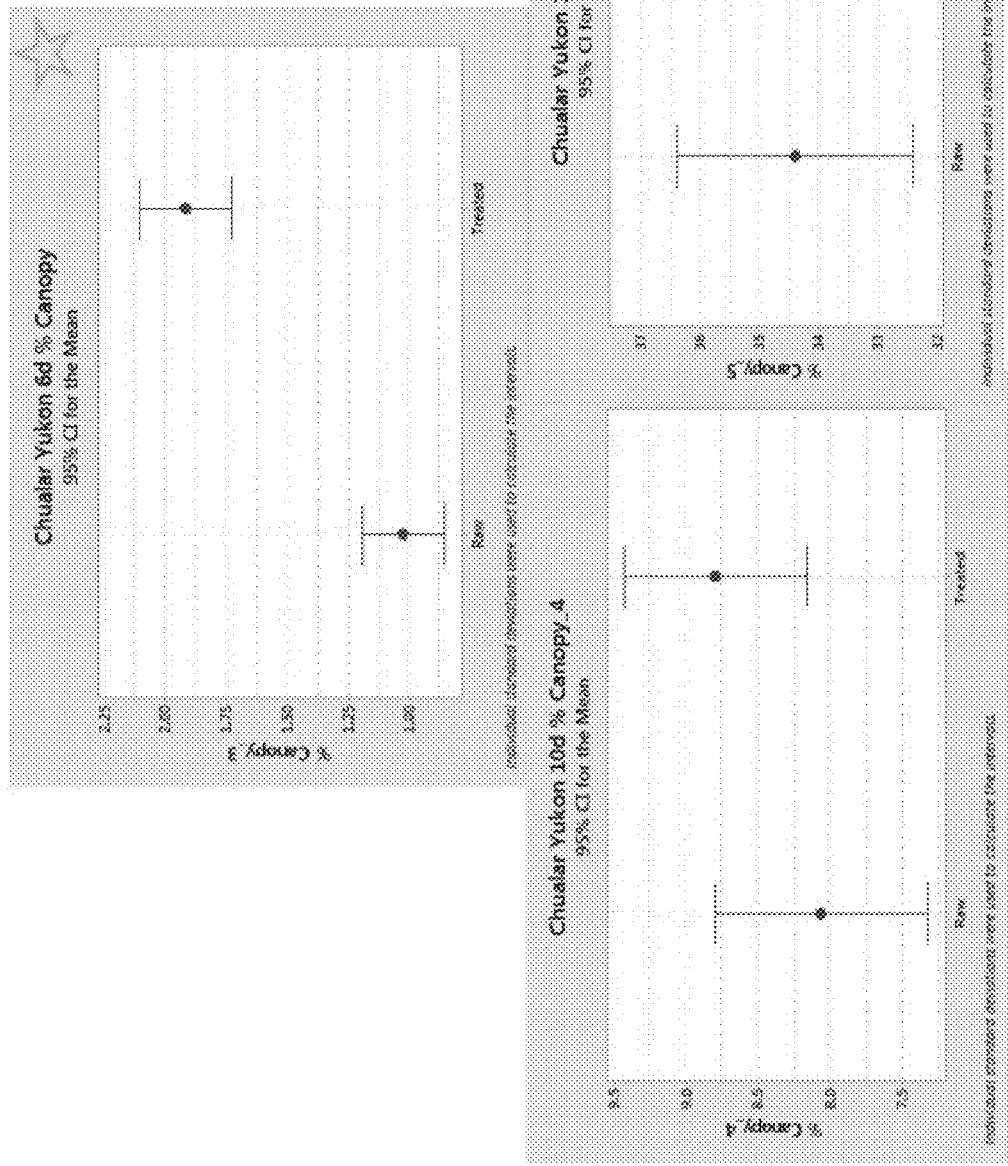

Image analysis of canopy coverage is shown in FIG. 9-13. Images shown in FIG. 9 and FIG. 10 were taken using software comparable to ImageJ or Canopeo (iPhone-compatible app), with reversal of image color to enable pixel count and subsequent area determination. As shown in FIGS. 11-13, early canopy development was significantly (P=0.05) faster with treated spinach seed. Treated Callisto and Yukon seed showed significantly (P=0.05) faster development during the first 10 days and 7 days, respectively. Canopy area development from treated seed showed more advantage at Halperin site (Example 2) due to higher soil-borne disease pressure there in comparison with Chular trial site.

Example 4

Peas

Pea seeds coated with the formulation of Example 1, except the amount of copper (II) hydroxide was varied, were planted in clean, non-inoculated potting soil as a control alongside treated seeds planted in field soil with known *Pythium Ultimum* fungal pathogen contamination. The seeds were coated with three different rates (3 wt. %-15 wt. % of copper (II) hydroxide) in the formulation of Example 1. The seedling emergence counts were evaluated on days 4 and 7 after planting. The number of healthy plants (no symptoms of basil root rot) were determined.

Rate 1 (3%): No efficacy observed, as indicated, only 1-2 plants emerged from the pathogen containing field soil.

TABLE 2

| | Example 1 formulation coated on Peas at 3% | | | | |
| --- | --- | --- | --- | --- | --- |
| Treatment | Soil Type | Rep | 4 DAP (16 seeds per rep) | Healthy (7 DAP) | Wilt/Dead (7 DAP) |
| Raw | Sunshine Mix | Rep 1 | 10 | 16 | |
| Raw | Sunshine Mix | Rep 2 | 15 | 16 | |
| Raw | Sunshine Mix | Rep 3 | 9 | 16 | |
| Raw | Sunshine Mix | Rep 4 | 13 | 14 | |
| Example 1 | Sunshine Mix | Rep 1 | 13 | 16 | |
| Example 1 | Sunshine Mix | Rep 2 | 13 | 16 | |
| Example 1 | Sunshine Mix | Rep 3 | 14 | 16 | |
| Example 1 | Sunshine Mix | Rep 4 | 14 | 16 | |
| Raw | Field Soil | Rep 1 | 0 | 0 | |
| Raw | Field Soil | Rep 2 | 0 | 0 | |
| Raw | Field Soil | Rep 3 | 0 | 0 | |
| Raw | Field Soil | Rep 4 | 0 | 0 | |
| Example 1 | Field Soil | Rep 1 | 0 | 0 | |
| Example 1 | Field Soil | Rep 2 | 2 | 1 | 1 |
| Example 1 | Field Soil | Rep 3 | 0 | 0 | |
| Example 1 | Field Soil | Rep 4 | 1 | 0 | 1 |

DAP means days after planting

Rate 2 (9%): Example 1 formulation on treated peas at three times the active ingredient concentration of rate 1 shows efficacy of the seed treatment with 56%-87% of the seeds planted growing, producing a non-symptomatic healthy plant compared to raw non-treated seeds.

TABLE 3

Example 1 formulation coated on Peas at 9%

| Treatment | Soil Type | Rep | 4 DAP (16 seeds per rep) | Healthy (7 DAP) | Wilt/Dead (7 DAP) |
|---|---|---|---|---|---|
| Raw | Sunshine Mix | Rep 1 | 11 | 16 | |
| Raw | Sunshine Mix | Rep 2 | 12 | 16 | |
| Raw | Sunshine Mix | Rep 3 | 12 | 16 | |
| Raw | Sunshine Mix | Rep 4 | 12 | 14 | |
| Example 1 | Sunshine Mix | Rep 1 | 13 | 14 | |
| Example 1 | Sunshine Mix | Rep 2 | 12 | 15 | |
| Example 1 | Sunshine Mix | Rep 3 | 12 | 16 | |
| Example 1 | Sunshine Mix | Rep 4 | 11 | 15 | |
| Raw | Field Soil | Rep 1 | 3 | 2 | 1 |
| Raw | Field Soil | Rep 2 | 2 | 2 | 1 |
| Raw | Field Soil | Rep 3 | 4 | 4 | 1 |
| Raw | Field Soil | Rep 4 | 0 | 0 | |
| Example 1 | Field Soil | Rep 1 | 14 | 13 | 1 |
| Example 1 | Field Soil | Rep 2 | 11 | 14 | |
| Example 1 | Field Soil | Rep 3 | 11 | 9 | 2 |
| Example 1 | Field Soil | Rep 4 | 5 | 12 | |

Rate 3 (15%): Example 1 formulation on treated peas at five times the active ingredient concentration of rate 1 shows the negative affect of the high concentration reducing the number of healthy plants emerging from the fungal contaminated field soil.

TABLE 4

Example 1 formulation coated on Peas at 15%

| Treatment | Soil Type | Rep | 4 dap (out of 16 seeds per rep) | Healthy (7 dap) | Wilt/Dead (7 dap) |
|---|---|---|---|---|---|
| Raw | Lab Soil | Rep 1 | 12 | 15 | |
| Raw | Lab Soil | Rep 2 | 14 | 16 | |
| Raw | Lab Soil | Rep 3 | 13 | 16 | |
| Raw | Lab Soil | Rep 4 | 10 | 15 | |
| Example 1 | Lab Soil | Rep 1 | 10 | 14 | |
| Example 1 | Lab Soil | Rep 2 | 12 | 14 | |
| Example 1 | Lab Soil | Rep 3 | 11 | 16 | |
| Example 1 | Lab Soil | Rep 4 | 12 | 15 | |
| Raw | Field Soil | Rep 1 | 1 | 1 | |
| Raw | Field Soil | Rep 2 | 0 | 0 | |
| Raw | Field Soil | Rep 3 | 0 | 0 | |
| Raw | Field Soil | Rep 4 | 0 | 0 | |
| Example 1 | Field Soil | Rep 1 | 3 | 9 | |
| Example 1 | Field Soil | Rep 2 | 2 | 8 | |
| Example 1 | Field Soil | Rep 3 | 7 | 7 | |
| Example 1 | Field Soil | Rep 4 | 10 | 11 | |

Example 5

Comparison with Cuprous Oxide

Pea seeds coated with the formulation of Example 1, at rate 2 (9% copper (II) hydroxide in the formulation), were planted in natural growing conditions for field peas in the Pacific Northwest. Pea seeds treated with Nordox, which contains cuprous oxide as the active ingredient, were planted in the same conditions. The pea seeds coated with the formulation of Example 1 produced 72% of the theoretical stand, while those treated with Nordox only produced 34% of the theoretical stand.

Example 6

Forage Corn

Forage corn was treated with three rates of the formulation of Example 1 (Corn 4 at 4%, corn 5 at 11%, and corn 6 at 17%). Table 5 shows data from one rate. Samples 17-20 show that that non-treated corn seed planted in field soil containing the fungal pathogen does not emerge and produce a stand. In contrast, the corn seeds treated with formulation of Example 1, Samples 21-32, have virtually the same number of plants growing when compared to corn grown in disease free potting mix.

TABLE 5

| Sample | Treatment | Soil Type | Rep | Healthy (9 DAP) | Healthy (14 DAP) | Healthy (21 DAP) |
|---|---|---|---|---|---|---|
| 1 | Raw | Peat Soil | Rep 1 | 0 | 21 | 25 |
| 2 | Raw | Peat Soil | Rep 2 | 0 | 22 | 25 |
| 3 | Raw | Peat Soil | Rep 3 | 0 | 23 | 24 |
| 4 | Raw | Peat Soil | Rep 4 | 0 | 25 | 25 |
| 5 | corn 4 | Peat Soil | Rep 1 | 0 | 21 | 24 |
| 6 | corn 4 | Peat Soil | Rep 2 | 0 | 20 | 23 |
| 7 | corn 4 | Peat Soil | Rep 3 | 0 | 11 | 25 |
| 8 | corn 4 | Peat Soil | Rep 4 | 0 | 15 | 24 |
| 9 | corn 5 | Peat Soil | Rep 1 | 0 | 24 | 25 |
| 10 | corn 5 | Peat Soil | Rep 2 | 0 | 24 | 24 |
| 11 | corn 5 | Peat Soil | Rep 3 | 0 | 12 | 25 |
| 12 | corn 5 | Peat Soil | Rep 4 | 0 | 23 | 24 |
| 13 | corn 6 | Peat Soil | Rep 1 | 0 | 24 | 23 |
| 14 | corn 6 | Peat Soil | Rep 2 | 0 | 20 | 24 |
| 15 | corn 6 | Peat Soil | Rep 3 | 0 | 24 | 25 |
| 16 | corn 6 | Peat Soil | Rep 4 | 0 | 20 | 18 |
| 17 | Raw | Field Soil | Rep 1 | 0 | 1 | 6 |
| 18 | Raw | Field Soil | Rep 2 | 0 | 5 | 8 |
| 19 | Raw | Field Soil | Rep 3 | 0 | 0 | 0 |
| 20 | Raw | Field Soil | Rep 4 | 0 | 0 | 3 |
| 21 | corn 4 | Field Soil | Rep 1 | 0 | 20 | 24 |
| 22 | corn 4 | Field Soil | Rep 2 | 0 | 11 | 17 |
| 23 | corn 4 | Field Soil | Rep 3 | 0 | 7 | 17 |
| 24 | corn 4 | Field Soil | Rep 4 | 0 | 4 | 19 |
| 25 | corn 5 | Field Soil | Rep 1 | 0 | 14 | 22 |
| 26 | corn 5 | Field Soil | Rep 2 | 0 | 21 | 24 |
| 27 | corn 5 | Field Soil | Rep 3 | 0 | 8 | 22 |
| 28 | corn 5 | Field Soil | Rep 4 | 0 | 14 | 22 |
| 29 | corn 6 | Field Soil | Rep 1 | 0 | 7 | 16 |
| 30 | corn 6 | Field Soil | Rep 2 | 0 | 4 | 16 |
| 31 | corn 6 | Field Soil | Rep 3 | 0 | 18 | 23 |
| 32 | corn 6 | Field Soil | Rep 4 | 0 | 17 | 21 |

A second replication of this trial with Corn 4, Corn 5, and Corn 6, treated rates of the formulation of Example 1 is shown in Table 6. Raw seed in diseased field soil not providing a stand while Corn 4, 5, and 6, all showing improved seedling emergence as the seed treatment is preventing root rot from occurring.

TABLE 6

| Sample | Treatment | Soil Type | Rep | Healthy (9 DAP) | Healthy (14 DAP) | Healthy (21 DAP) |
|---|---|---|---|---|---|---|
| 33 | Raw | Peat Soil | Rep 1 | 0 | 21 | 25 |
| 34 | Raw | Peat Soil | Rep 2 | 0 | 22 | 25 |
| 35 | Raw | Peat Soil | Rep 3 | 0 | 23 | 24 |
| 36 | Raw | Peat Soil | Rep 4 | 0 | 25 | 25 |
| 37 | corn 4 | Peat Soil | Rep 1 | 0 | 21 | 24 |
| 38 | corn 4 | Peat Soil | Rep 2 | 0 | 20 | 23 |
| 39 | corn 4 | Peat Soil | Rep 3 | 0 | 11 | 25 |
| 40 | corn 4 | Peat Soil | Rep 4 | 0 | 15 | 24 |
| 41 | corn 5 | Peat Soil | Rep 1 | 0 | 24 | 25 |
| 42 | corn 5 | Peat Soil | Rep 2 | 0 | 24 | 24 |
| 43 | corn 5 | Peat Soil | Rep 3 | 0 | 12 | 25 |
| 44 | corn 5 | Peat Soil | Rep 4 | 0 | 23 | 24 |
| 45 | corn 6 | Peat Soil | Rep 1 | 0 | 24 | 23 |
| 46 | corn 6 | Peat Soil | Rep 2 | 0 | 20 | 24 |
| 47 | corn 6 | Peat Soil | Rep 3 | 0 | 24 | 25 |
| 48 | corn 6 | Peat Soil | Rep 4 | 0 | 20 | 18 |
| 49 | Raw | Field Soil | Rep 1 | 0 | 1 | 6 |

TABLE 6-continued

| Sample | Treatment | Soil Type | Rep | Healthy (9 DAP) | Healthy (14 DAP) | Healthy (21 DAP) |
|---|---|---|---|---|---|---|
| 50 | Raw | Field Soil | Rep 2 | 0 | 5 | 8 |
| 51 | Raw | Field Soil | Rep 3 | 0 | 0 | 0 |
| 52 | Raw | Field Soil | Rep 4 | 0 | 0 | 3 |
| 53 | corn 4 | Field Soil | Rep 1 | 0 | 20 | 24 |
| 54 | corn 4 | Field Soil | Rep 2 | 0 | 11 | 17 |
| 55 | corn 4 | Field Soil | Rep 3 | 0 | 7 | 17 |
| 56 | corn 4 | Field Soil | Rep 4 | 0 | 4 | 19 |
| 57 | corn 5 | Field Soil | Rep 1 | 0 | 14 | 22 |
| 58 | corn 5 | Field Soil | Rep 2 | 0 | 21 | 24 |
| 59 | corn 5 | Field Soil | Rep 3 | 0 | 8 | 22 |
| 60 | corn 5 | Field Soil | Rep 4 | 0 | 14 | 22 |
| 61 | corn 6 | Field Soil | Rep 1 | 0 | 7 | 16 |
| 62 | corn 6 | Field Soil | Rep 2 | 0 | 4 | 16 |
| 63 | corn 6 | Field Soil | Rep 3 | 0 | 18 | 23 |
| 64 | corn 6 | Field Soil | Rep 4 | 0 | 17 | 21 |

In summary, the data collected to date indicates that the seed treatment formulation has a very strong efficacy against the soil fungal pathogen *Pythium*. This has been demonstrated on leafy green vegetables species such as organic spinach, field peas, and forage corn. it is believed that the efficacy of this seed treatment will apply to other species such as soybeans, which when grown organically are prone to crop losses from this soil pathogen.

What is claimed is:

1. A coated seed comprising:
a seed and
a coating at least partially surrounding the seed,
wherein the coating comprises a fungicide, a micronutrient metal, and a chelating agent, the fungicide comprising copper (II) hydroxide, wherein the amount of copper (II) hydroxide is from about 0.12 mg/seed to about 0.21 mg/seed; wherein the micronutrient metal comprises zinc; and wherein the chelating agent comprises zeolite.

2. The coated seed of claim 1, wherein the micronutrient further comprises a metal selected from manganese, iron, boron, chromium, cobalt, copper, and salts thereof.

3. The coated seed of claim 1, wherein the micronutrient comprises one or more zinc salt.

4. The coated seed of claim 1, wherein the chelating agent is selected from the group consisting of zeolite and EDTA.

5. The coated seed of claim 1, wherein the coating further comprises a binding agent.

6. The coated seed of claim 5, wherein the binding agent is selected from the group consisting of a fiber gum and polyvinyl alcohol.

7. The coated seed of claim 1, wherein the coating further comprises humic acid.

8. The coated seed of claim 1, wherein the coating is substantially free of added fulvic acid.

9. The coated seed of claim 1, wherein the coating further comprises a soil conditioner.

10. The coated seed of claim 1, wherein the coating further comprises a bactericide.

11. The coated seed of claim 1, wherein the coating has a pH in the range of 6.0 to 6.4.

12. The coated seed of claim 1, wherein the coating encapsulates the seed.

13. The coated seed of claim 1, wherein the seed is a spinach, pea, or corn seed.

14. A method for applying a seed treatment to a seed or a population of seeds, the method comprising:
distributing on the surface of the seed or the population of seeds a seed treatment formulation comprising a fungicide, a micronutrient metal, and a chelating agent, and
drying the seed treatment formulation to form a coating, wherein the fungicide comprises copper (II) hydroxide in an amount anging from about 9 wt. % to about 20 wt. % of the total seed treatment formulation.

15. The method of claim 14, wherein the seed treatment formulation is a liquid slurry.

16. The method of claim 14, wherein the seed treatment formulation further comprises a coloring agent.

17. A method of protecting an emerging root system from fungal infection, the method comprising
providing at least one seed,
coating the at least one seed with a seed treatment formulation comprising fungicide, a micronutrient metal, and a chelating agent,
drying the seed treatment formulation to form a coating, and
planting the coated seed under conditions suitable for germination,
wherein the fungicide comprises copper (II) hydroxide wherein the amount of copper (II) hydroxide comprises at least about 9 wt. % and no more than about 20 wt. % of the total seed treatment formulation.

18. The method of claim 17, wherein the coated seed comprises a spinach, pea, or corn seed.

19. The method of claim 17, wherein the coating is effective to protect the emerging root system from fungal infection for at least 5 days.

20. The method of claim 17, wherein the conditions are an organic growing medium.

* * * * *